US012576100B2

(12) United States Patent
Lotem et al.

(10) Patent No.: US 12,576,100 B2
(45) Date of Patent: Mar. 17, 2026

(54) NUCLEIC ACID AGENTS MODULATING SLAMF6 ISOFORMS

(71) Applicant: HADASIT MEDICAL RESEARCH SERVICES AND DEVELOPMENT LTD., Jerusalem (IL)

(72) Inventors: Michal Lotem, Reut (IL); Emma Hajaj, Netanya (IL); Galit Eisenberg, Modiin (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 1116 days.

(21) Appl. No.: 17/622,224

(22) PCT Filed: Jun. 23, 2020

(86) PCT No.: PCT/IL2020/050697
§ 371 (c)(1),
(2) Date: Dec. 22, 2021

(87) PCT Pub. No.: WO2020/261265
PCT Pub. Date: Dec. 30, 2020

(65) Prior Publication Data
US 2022/0347203 A1     Nov. 3, 2022

Related U.S. Application Data

(60) Provisional application No. 62/882,625, filed on Aug. 5, 2019.

(30) Foreign Application Priority Data

Jun. 24, 2019    (IL) ......................................... 267614

(51) Int. Cl.
| | |
|---|---|
| *A61K 40/32* | (2025.01) |
| *A61K 31/712* | (2006.01) |
| *A61K 38/17* | (2006.01) |
| *A61K 39/395* | (2006.01) |
| *A61K 40/11* | (2025.01) |
| *A61K 40/42* | (2025.01) |
| *A61P 35/00* | (2006.01) |
| *C12N 15/113* | (2010.01) |

(52) U.S. Cl.
CPC ........ *A61K 31/712* (2013.01); *A61K 38/1774* (2013.01); *A61K 39/3955* (2013.01); *A61K 40/11* (2025.01); *A61K 40/32* (2025.01); *A61K 40/4269* (2025.01); *A61P 35/00* (2018.01); *C12N 15/1138* (2013.01); *A61K 2239/57* (2023.05)

(58) Field of Classification Search
CPC .............................. C12N 15/113; A61K 40/32
See application file for complete search history.

(56) References Cited

U.S. PATENT DOCUMENTS

| | | | |
|---|---|---|---|
| 4,376,110 | A | 3/1983 | David |
| 4,522,811 | A | 6/1985 | Eppstein |
| 4,816,567 | A | 3/1989 | Cabilly |
| 5,225,539 | A | 7/1993 | Winter |
| 5,436,330 | A | 7/1995 | Taira |
| 5,545,729 | A | 8/1996 | Goodchild |
| 5,545,807 | A | 8/1996 | Surani |
| 5,631,115 | A | 5/1997 | Ohtsuka |
| 5,693,761 | A | 12/1997 | Queen |
| 5,693,762 | A | 12/1997 | Queen |
| 6,277,981 | B1 | 8/2001 | Tu |
| 6,284,267 | B1 | 9/2001 | Aneja |
| 6,660,843 | B1 | 12/2003 | Feige |
| 6,887,470 | B1 | 5/2005 | Bridon |
| 6,926,898 | B2 | 8/2005 | Rosen |
| 6,972,171 | B1 | 12/2005 | Schlingensiepen |
| 7,022,832 | B2 | 4/2006 | Malvy |
| 7,592,313 | B2 | 9/2009 | Zheng |
| 2003/0180888 | A1* | 9/2003 | Fraser .................... G01N 33/53 |
| | | | 435/69.1 |
| 2003/0191056 | A1 | 10/2003 | Walker |
| 2003/0195154 | A1 | 10/2003 | Walker |
| 2005/0054051 | A1 | 3/2005 | Rosen |
| 2005/0261485 | A1 | 11/2005 | Uchida |
| 2006/0099177 | A1 | 5/2006 | June |
| 2009/0017014 | A1 | 1/2009 | Valdez |
| 2009/0181009 | A1 | 7/2009 | Abo |

(Continued)

FOREIGN PATENT DOCUMENTS

| | | |
|---|---|---|
| EP | 2083088 A2 | 7/2009 |
| JP | 2005-206478 A | 8/2005 |

(Continued)

OTHER PUBLICATIONS

Korver et al. (2007) "The lymphoid cell surface receptor NTB-A: a novel monoclonal antibody target for leukaemia and lymphoma therapeutics" British journal of haematology, 137(4), 307-318. (Year: 2007).*

GenBank AJ306388.1, "*Homo sapiens* mRNA for NTB-A receptor (KALI b gene)", entered: Oct. 7, 2008, National Library of Medicine (US), National Center for Biotechnology Information. (Year: 2008).*

Hajaj et al. (2021) "Alternative splicing of the inhibitory immune checkpoint receptor SLAMF6 generates a dominant positive form, boosting T-cell effector functions" Cancer immunology research, 9(6), 637-650. (Year: 2021).*

(Continued)

*Primary Examiner* — James Joseph Graber

(74) *Attorney, Agent, or Firm* — FULLER IP LAW LLC; Rodney J. Fuller

(57) ABSTRACT

The invention relates to nucleic acid agents modulating the expression of SLAMF6 isoforms, compositions comprising same and methods for their use in immunomodulation. Specifically, provided are splice-switching oligonucleotides and constructs useful in cancer immunotherapy.

21 Claims, 9 Drawing Sheets

Specification includes a Sequence Listing.

(56)                    References Cited

U.S. PATENT DOCUMENTS

| | | | |
|---|---|---|---|
| 2010/0150886 | A1 | 6/2010 | Marui |
| 2011/0160642 | A1 | 6/2011 | Neuberger |
| 2011/0171204 | A1 | 7/2011 | Abo |
| 2012/0244133 | A1 | 9/2012 | Rosenberg |
| 2014/0068797 | A1 | 3/2014 | Doudna |
| 2014/0302070 | A1 | 10/2014 | Chen |
| 2016/0311907 | A1 | 10/2016 | Brogdon |
| 2016/0333072 | A1 | 11/2016 | Rutenberg |
| 2017/0334989 | A1 | 11/2017 | Abo |
| 2019/0040136 | A1 | 2/2019 | Wang |

FOREIGN PATENT DOCUMENTS

| | | | |
|---|---|---|---|
| WO | 8601533 | A1 | 3/1986 |
| WO | 9007861 | A1 | 7/1990 |
| WO | 9702671 | A2 | 1/1997 |
| WO | 03008449 | A1 | 1/2003 |
| WO | 2006006948 | A2 | 1/2006 |
| WO | 2006037421 | A2 | 4/2006 |
| WO | 2007045996 | A1 | 4/2007 |
| WO | 2012156969 | A1 | 11/2012 |
| WO | 2014093701 | A1 | 6/2014 |
| WO | 2015104711 | A1 | 7/2015 |
| WO | 2016201394 | A1 | 12/2016 |
| WO | 2017019894 | A1 | 2/2017 |
| WO | 2017075478 | A2 | 5/2017 |
| WO | 2018020476 | A1 | 2/2018 |
| WO | 2018049025 | A2 | 3/2018 |
| WO | 2018112470 | A1 | 6/2018 |
| WO | 2019155474 | A1 | 8/2019 |
| WO | 2020261266 | A1 | 12/2020 |

OTHER PUBLICATIONS

Hajaj et al. (Aug. 22, 2020) "Alternative splicing of SLAMF6 in human T cells creates a co-stimulatory isoform that counteracts the inhibitory effect of the full-length receptor" bioRxiv, pre-print, 33 pages. (Year: 2020).*

Themeli et al., (2015) New cell sources for T cell engineering and adoptive immunotherapy. Cell Stem Cell 16(4): 357-366.

Yigit et al., (2016) A combination of an anti-SLAMF6 antibody and ibrutinib efficiently abrogates expansion of chronic lymphocytic leukemia cells. Oncotarget 7(18): 26346-26360.

Ayers et al., (2017) IFN-γ-related mRNA profile predicts clinical response to PD-1 blockade. J Clin Invest 127(8): 2930-2940.

Bendig (1995) Humanization of rodent monoclonal antibodies by CDR grafting. Methods: A Companion to Methods in Enzymology 8: 83-93.

Chatterjee et al., (2011) SLAMF6-driven co-stimulation of human peripheral T cells is defective in SLE T cells. Autoimmunity 44(3): 211-218; pp. 1-14.

Choo et al., (2009) A comprehensive assessment of N-terminal signal peptides prediction methods. BMC Bioinformatics 10 Suppl 15(Suppl 15): S2, pp. 1-12.

Colman (1994) Effects of amino acid sequence changes on antibody-antigen interactions. Res Immunol 145(1): 33-36.

Crawford et al., (2004) Chemotherapy-induced neutropenia: risks, consequences, and new directions for its management. Cancer 100(2): 228-237.

Dutta and Schwartzberg (2012) Characterization of Ly108 in the thymus: evidence for distinct properties of a novel form of Ly108. J Immunol 188(7): 3031-3041.

Eisenberg et al., (2018) Soluble SLAMF6 Receptor Induces Strong CD8+ T-cell Effector Function and Improves Anti-Melanoma Activity In Vivo. Cancer Immunol Res 6(2): 127-138.

Elflein et al., (2003) Rapid recovery from T lymphopenia by CD28 superagonist therapy. Blood 102(5): 1764-1770.

Falco et al., (2004) Homophilic interaction of NTBA, a member of the CD2 molecular family: induction of cytotoxicity and cytokine release in human NK cells. Eur J Immunol 34(6): 1663-1672.

Fv Structure and Diversity in Three Dimensions. In: Fundamental Immunology, edited by Paul We. Raven Press, New York, USA. 1993; pp. 292-295.

Hajaj et al., (2018) Diverse effects of the splice isoforms of immune receptor SLAMF6—a new regulatory mechanism. EACR-AACR-ISCR Conference: The Cutting Edge of Contemporary Cancer Research, Oct. 9-11, 2018, Jerusalem, Israel. 1 page.

Hajaj et al., (2020) SLAMF6 deficiency augments tumor killing and skews toward an effector phenotype revealing it as a novel T cell checkpoint. Elife 9: e52539; 23 pages.

Hajaj et al., (2021) Alternative Splicing of the Inhibitory Immune Checkpoint Receptor SLAMF6 Generates a Dominant Positive Form, Boosting T-cell Effector Functions. Cancer Immunol Res 9(6): 637-650.

Hanawa et al., (2002) A novel costimulatory signaling in human T lymphocytes by a splice variant of CD28. Blood 99 (6): 2138-2145.

Havens and Hastings (2016) Splice-switching antisense oligonucleotides as therapeutic drugs. Nucleic Acids Res 44 (14): 6549-6563.

Ji et al., (2014) Identification of the genomic insertion site of Pmel-1 TCR α and β transgenes by next-generation sequencing. PLoS One 9(5): e96650; 8 pages.

Jiang et al., (2016) Role of IL-2 in cancer immunotherapy. Oncoimmunology 5(6): e1163462.

Keszei et al., (2011) A novel isoform of the Ly108 gene ameliorates murine lupus. J Exp Med 208(4): 811-822.

Khantasup et al., (2015) Design and Generation of Humanized Single-chain Fv Derived from Mouse Hybridoma for Potential Targeting Application. Monoclon Antib Immunodiagn Immunother 34(6): 404-417.

Korver et al., (2007) The lymphoid cell surface receptor NTB-A: a novel monoclonal antibody target for leukaemia and lymphoma therapeutics. British Journal of Haematology 137(4): 307-318.

Korver et al., (2008) Potent Anti-Cancer Activity of Anti-NTB-a Monoclonal Antibodies in Preclinical Leukemia and Lymphoma Models. Blood 112 (11): 4975.

Kozlovski et al., (2017) The role of RNA alternative splicing in regulating cancer metabolism. Hum Genet 136(9): 1113-1127.

Kumar et al., (2018) A comprehensive review on the role of co-signaling receptors and Treg homeostasis in autoimmunity and tumor immunity. J Autoimmun. Author manuscript; available in PMC Dec. 1, 2019. Published in final edited form as: J Autoimmun. Dec. 2018; 95: 77-99.

Long et al., (2018) The promising immune checkpoint LAG-3: from tumor microenvironment to cancer immunotherapy. Genes Cancer 9(5-6): 176-189.

Martin and Sawyer (2019) Elucidating the structure of membrane proteins. Tech News, BioTechniques 66(4): 167-170.

Miller et al., (2019) Subsets of exhausted CD8+ T cells differentially mediate tumor control and respond to checkpoint plockade. Nat Immunol. Author manuscript; available in PMC Aug. 1, 2019. Published in final edited form as: Nat Immunol. Mar. 2019; 20(3): 326-336.

Ni and Lu (2018) Interferon gamma in cancer immunotherapy. Cancer Med 7(9): 4509-4516.

Oberdoerffer et al., (2008) Regulation of CD45 alternative splicing by heterogeneous ribonucleoprotein, hnRNPLL. Science 321(5889): 686-691.

Ota et al., (2004) Complete sequencing and characterization of 21,243 full-length human cDNAs. Nat Genet 36(1): 40-45.

Overwijk et al., (2003) Tumor regression and autoimmunity after reversal of a functionally tolerant state of self-reactive CD8+ T cells. J Exp Med 198(4): 569-580.

Rudikoff et al., (1982) Single amino acid substitution altering antigen-binding specificity. Proc Natl Acad Sci U S A 79(6): 1979-1983.

Rutenberg et al., (2013) NTB-A receptor potentiates anti-cancer activity of cytotoxic t lymphocytes and represents a potential druggable target for cancer immunotherapy. The Fifth Annual Meeting of the Israeli Society for Cancer Research (ISCR). The 2013 Cancer Route-Stem Cells, the Microenvironment, Gene Regulation and Novel Therapies. May 23, 2013, Ben Gurion University of the Negev, Israel. 2 pages.

(56) References Cited

OTHER PUBLICATIONS

Snow et al., (2009) Restimulation-induced apoptosis of T cells is impaired in patients with X-linked lymphoproliferative disease caused by SAP deficiency. The Journal of Clinical Investigation 119(10): 2976-2989.

Snow et al., (2010) The power and the promise of restimulation-induced cell death in human immune diseases. Immunological Reviews 236(1): 68-82.

Uzana et al., (2012) Trogocytosis is a gateway to characterize functional diversity in melanoma-specific CD8+ T cell clones. J Immunol 188(2): 632-640.

Valdez et al., (2004) NTB-A, a new activating receptor in T cells that regulates autoimmune disease. J Biol Chem 279(18): 18662-18669.

Wang and Burge (2008) Splicing regulation: from a parts list of regulatory elements to an integrated splicing code. RNA 14(5): 802-813.

Wang and Cooper (2007) Splicing in disease: disruption of the splicing code and the decoding machinery. Nat Rev Genet 8(10): 749-761.

Waugh et al., (2016) Molecular Profile of Tumor-Specific CD8+ T Cell Hypofunction in a Transplantable Murine Cancer Model. J Immunol 197(4): 1477-1488.

Wu et al., (2012) Adoptive T-Cell Therapy Using Autologous Tumor-Infiltrating Lymphocytes for Metastatic Melanoma: Current Status and Future Outlook. The Cancer Journal 18(2): 160-175.

Wu et al., (2016) A hematopoietic cell-driven mechanism involving SLAMF6 receptor, SAP adaptors and SHP-1 phosphatase regulates NK cell education. Nat Immunol, published online Feb. 15, 2016; doi:10.1038/ni.3369; 11 pages. Published in final version as: Nat Immunol 17(4): 387-396.

Yigit (2018) SLAMF6 is a checkpoint inhibitor of CD8+ T cell exhaustion in Chronic Lymphocytic Leukemia. SLAMF Receptors In Health and Disease: Implications for Therapeutic Targeting, 87, Dec. 31, 2018 (Dec. 31, 2018). Doctoral Thesis Utrecht University, the Netherlands. 177 pages.

Yigit et al., (2019) SLAMF6 as a Regulator of Exhausted CD8+ T Cells in Cancer. Cancer Immunol Res 7(9): 1485-1496.

Yigit et al., (2019) SLAMF6 in health and disease: Implications for therapeutic targeting. Author's manuscript. Published in final edited format as: Clin Immunol 204: 3-13.

Database UniProt [Online]. Sep. 23, 2008 (Sep. 23, 2009), "SubName: Full=cDNA FLJ52047, highly similar to SLAM family member 6 {ECO:0000313 | EMBL:BAG64907.1};", XP002804381. Retrieved from EBI accession No. UNIPROT:B4E1U5. Database accession No. B4E1U5, *sequence*.

NCBI Reference Sequence: XP_004027766.1. Predicted: SLAM family member 6 isoform X3 [Gorilla gorilla gorilla] REFSEQ: accession XM_004027717.2 Publication Date: Nov. 4, 2016. Retrieved from the Internet on: Apr. 16, 2019.

NCT00612664, first posted on Jan. 30, 2008. History of Changes for study: NCT00612664; Phase II, 2nd Line Melanoma—RAND Monotherapy. Retrieved from: https://clinicaltrials.gov/ct2/history/NCT00612664?A=1&B=1&C=merged#StudyPageTop on Mar. 30, 2022. 9 pages.

Bottino et al., (2001) NTB-A [correction of GNTB-A], a novel SH2D1A-associated surface molecule contributing to the nability of natural killer cells to kill Epstein-Barr virus-infected B cells in X-linked lymphoproliferative disease. J Exp Med 194(3): 235-246.

Eisenberg et al., (2014) Discovery of the immune modulatory role of SLAMF6 trough tumor-CD8-cell interactions; p. 80 [online], [retrieved on Apr. 2, 2015]. Retrieved from the Internet http://www.iscr.org.il/image/users/124131/ftp/my_files/pdf/%D7%A4%D7%95%D7%A1%D7%98%D7%A8%D7%99%D7%9D%20%D7%95%D7%AA%D7%A7%D7%A6%D7%99% D7%A8%D7%99%D7%9D%20%D7%9C%D7%90%D7%AA%D7%A8%20%D7%9E%D7%A2%D7%95%D7%93%D7%9B%D7%9F.pdf?id=16323521.

Hajaj et al., (2020) Alternative splicing of SLAMF6 in human T cells creates a co-stimulatory isoform that counteracts the inhibitory effect of the full-length receptor. bioRxiv 2020.08.21.262238; doi: https://doi.org/10.1101/2020.08.21.262238.

Kageyama et al., (2012) The receptor Ly108 functions as a SAP adaptor-dependent on-off switch for T cell help to B cells and NKT cell development. Immunity 36(6): 986-1002.

NCBI Reference Sequence: NM_001184715.1; *Homo sapiens* SLAM family member 6 (SLAMF6), transcript variant 3, MRNA. Retrieved from: https://www.ncbi.nlm.nih.gov/nuccore/NM_001184715.1 on Jul. 13, 2022. 4 pages.

NCBI Reference Sequence: NM_001184716.1; *Homo sapiens* SLAM family member 6 (SLAMF6), transcript variant 4, mRNA. Retrieved from: https://www.ncbi.nlm.nih.gov/nuccore/NM_001184716.1 on Jul. 15, 2022. 4 pages.

UniProt database entry Q96DU3; SLAF6_HUMAN. SLAM family member 6, *Homo sapiens* (Human), Gene: SLAMF6 (KALI). Retrieved from: https://www.uniprot.org/uniprotkb/Q96DU3/entry on Jul. 9, 2022. 10 pages.

Freund et al., (2022) Efficient synthesis and evolution of 2'-modified nucleic acid chemistries found in FDA-approved nucleic acid therapeutics. Published in Nature Chemistry, Behind the Paper. Oct. 13, 2022 (Oct. 13, 2022). Retrieved from: https://communities.springernature.com/posts/efficient-synthesis-and-evolution-of-2-modified-nucleic-acid-chemistries-found-in-fda-approved-nucleic-acid-therapeutics, on Feb. 3, 2025. 8 pages.

Castro et al., (2018) Interferon-Gamma at the Crossroads of Tumor Immune Surveillance or Evasion. Front Immunol 9:847.

Rezaei et al., (2010) X-linked lymphoproliferative syndrome: a genetic condition typified by the triad of infection, immunodeficiency and lymphoma. Br J Haematol 152(1):13-30.

Xu et al., (2014) LSECtin expressed on melanoma cells promotes tumor progression by inhibiting antitumor T-cell responses. Cancer Res 74(13):3418-3428.

Yigit et al., (2019) SLAMF6 in health and disease: Implications for therapeutic targeting. Clin Immunol 204:3-13.

Hajaj, et al., (2018) Diverse effects of the splice isoforms of immune receptor SLAMF6—a new regulatory mechanism. EACCR-AACR-ISCR Conference: The cutting edge of contemporary cancer research, Oct. 9-11, 2018, Jersualem, Israel, all enclosed pages cited.

Hajaj et al., (2018) SLAMF6 is a regulatory receptor for T cell activation. Cell-Weizmann Institute of Science Symposium: Next Gen Immunology. Poster Session 1 Sunday, Feb. 11, 2018; Immunity at Epithelial Barriers/Host Cell Microbe Interactions [P2.1.56]. Hadassah Hebrew University Medical Center, Israel, all enclosed pages cited.

* cited by examiner

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ggguacuaug aaggcaagag                                                    20

<210> SEQ ID NO 2
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 2
ucauggggua cuaugaaggc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ugguuucaug ggguacuaug                                              20

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 4
atctcttgcc ttcatagtac cccatgaaa                                   29

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tgaccgaaaa gucatcucaa                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ctcttgcctt catagtaccc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gccttcatag taccccatga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
catagtaccc catgaaacca                                              20

-continued

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
uugugaaacu acauucccug                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cagggaatgt agtttcacaa                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gcggaaagca tgttgtggct g                                            21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
ggagacagtg aggtttggct g                                            21

<210> SEQ ID NO 13
<211> LENGTH: 332
<212> TYPE: PRT
<213> ORGANISM: Homo sapiens

<400> SEQUENCE: 13

Met Leu Trp Leu Phe Gln Ser Leu Leu Phe Val Phe Cys Phe Gly Pro
1               5                   10                  15

Gly Asn Val Val Ser Gln Ser Ser Leu Thr Pro Leu Met Val Asn Gly
            20                  25                  30

Ile Leu Gly Glu Ser Val Thr Leu Pro Leu Glu Phe Pro Ala Gly Glu
        35                  40                  45

Lys Val Asn Phe Ile Thr Trp Leu Phe Asn Glu Thr Ser Leu Ala Phe
    50                  55                  60

Ile Val Pro His Glu Thr Lys Ser Pro Glu Ile His Val Thr Asn Pro
65                  70                  75                  80

Lys Gln Gly Lys Arg Leu Asn Phe Thr Gln Ser Tyr Ser Leu Gln Leu
                85                  90                  95

Ser Asn Leu Lys Met Glu Asp Thr Gly Ser Tyr Arg Ala Gln Ile Ser
            100                 105                 110

Thr Lys Thr Ser Ala Lys Leu Ser Ser Tyr Thr Leu Arg Ile Leu Arg
        115                 120                 125

-continued

```
Gln Leu Arg Asn Ile Gln Val Thr Asn His Ser Gln Leu Phe Gln Asn
    130                 135                 140

Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
                180                 185                 190

Tyr Thr Cys Ile Ala Glu Asn Ala Val Ser Asn Leu Ser Phe Ser Val
                195                 200                 205

Ser Ala Gln Lys Leu Cys Glu Asp Val Lys Ile Gln Tyr Thr Asp Thr
    210                 215                 220

Lys Met Ile Leu Phe Met Val Ser Gly Ile Cys Ile Val Phe Gly Phe
225                 230                 235                 240

Ile Ile Leu Leu Leu Leu Val Leu Arg Lys Arg Arg Asp Ser Leu Ser
                245                 250                 255

Leu Ser Thr Gln Arg Thr Gln Gly Pro Ala Glu Ser Ala Arg Asn Leu
                260                 265                 270

Glu Tyr Val Ser Val Ser Pro Thr Asn Asn Thr Val Tyr Ala Ser Val
                275                 280                 285

Thr His Ser Asn Arg Glu Thr Glu Ile Trp Thr Pro Arg Glu Asn Asp
    290                 295                 300

Thr Ile Thr Ile Tyr Ser Thr Ile Asn His Ser Lys Glu Ser Lys Pro
305                 310                 315                 320

Thr Phe Ser Arg Ala Thr Ala Leu Asp Asn Val Val
                325                 330

<210> SEQ ID NO 14
<211> LENGTH: 281
<212> TYPE: PRT
<213> ORGANISM: Homo sapiens

<400> SEQUENCE: 14

Met Leu Trp Leu Phe Gln Ser Leu Leu Phe Val Phe Cys Phe Gly Pro
1               5                   10                  15

Val Pro His Glu Thr Lys Ser Pro Glu Ile His Val Thr Asn Pro Lys
                20                  25                  30

Gln Gly Lys Arg Leu Asn Phe Thr Gln Ser Tyr Ser Leu Gln Leu Ser
        35                  40                  45

Asn Leu Lys Met Glu Asp Thr Gly Ser Tyr Arg Ala Gln Ile Ser Thr
    50                  55                  60

Lys Thr Ser Ala Lys Leu Ser Ser Tyr Thr Leu Arg Ile Leu Arg Gln
65                  70                  75                  80

Leu Arg Asn Ile Gln Val Thr Asn His Ser Gln Leu Phe Gln Asn Met
                85                  90                  95

Thr Cys Glu Leu His Leu Thr Cys Ser Val Glu Asp Ala Asp Asp Asn
                100                 105                 110

Val Ser Phe Arg Trp Glu Ala Leu Gly Asn Thr Leu Ser Ser Gln Pro
                115                 120                 125

Asn Leu Thr Val Ser Trp Asp Pro Arg Ile Ser Ser Glu Gln Asp Tyr
    130                 135                 140

Thr Cys Ile Ala Glu Asn Ala Val Ser Asn Leu Ser Phe Ser Val Ser
145                 150                 155                 160

Ala Gln Lys Leu Cys Glu Asp Val Lys Ile Gln Tyr Thr Asp Thr Lys
                165                 170                 175
```

-continued

```
Met Ile Leu Phe Met Val Ser Gly Ile Cys Ile Val Phe Gly Phe Ile
        180                 185                 190

Ile Leu Leu Leu Leu Val Leu Arg Lys Arg Arg Asp Ser Leu Ser Leu
        195                 200                 205

Ser Thr Gln Arg Thr Gln Gly Pro Glu Ser Ala Arg Asn Leu Glu Tyr
        210                 215                 220

Val Ser Val Ser Pro Thr Asn Asn Thr Val Tyr Ala Ser Val Thr His
225                 230                 235                 240

Ser Asn Arg Glu Thr Glu Ile Trp Thr Pro Arg Glu Asn Asp Thr Ile
                245                 250                 255

Thr Ile Tyr Ser Thr Ile Asn His Ser Lys Glu Ser Lys Pro Thr Phe
                260                 265                 270

Ser Arg Ala Thr Ala Leu Asp Asn Val
        275                 280
```

```
<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
tttgacggtg agaacatgta                                            20

<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
gaatgttgaa gtcttcactt t                                          21

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
tcttcttgga tagagacacc                                            20

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
gccttcgctt acaagcactg                                            20

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
```

-continued

```
atcaaggcgg agaggaagcg                                        20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
tgagcatgtt ggccgtggac                                        20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tcatgaagaa ccaggtggcc                                        20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
atggtcaggg tgaaactctt                                        20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ccaagtacta tgagctggcc                                        20

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 24
cctcgaccgc ctcttcttc                                         19

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
aacacgcata tctttacttt                                        20

<210> SEQ ID NO 26
<211> LENGTH: 20
<212> TYPE: DNA
```

-continued

```
<213> ORGANISM: Artificial Sequence
<220> FEATURE:
<223> OTHER INFORMATION: Synthetic oligonucleotide

<400> SEQUENCE: 26
tcaattttca gctgagtaat                                            20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tggcctgttc tatagcatct                                            20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
tacatgaagt ccaggaggat                                            20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gtgaggtccg ttaggaaaaa                                            20

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
gttcatgttg tatagcaggc t                                          21

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
tgtgggctct actacaagct tcac                                       24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
gctagacatt tttcggtttc tggt                                       24
```

-continued

```
<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
gaggatttgg aaagggtgtt t                                             21

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
catctcgagc aagacgttca                                               20
```

NUCLEIC ACID AGENTS MODULATING SLAMF6 ISOFORMS

CROSS-REFERENCE TO RELATED APPLICATIONS

This application is the U.S. National Stage of International Patent Application No. PCT/IL2020/050697, filed on Jun. 23, 2020, which claims the benefit of and priority to U.S. Provisional Patent Application No. 62/882,625, filed on Aug. 5, 2019, and Israel Patent Application No. 267614, filed on Jun. 24, 2019, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 11,973 byte ASCII (text) file named "Seq_List" created on Jun. 12, 2020.

FIELD OF THE INVENTION

The invention relates to nucleic acid agents modulating the expression of SLAMF6 isoforms, and methods of using same in immunotherapy and immunomodulation.

BACKGROUND OF THE INVENTION

SLAMF6, a member of the SLAM (signaling lymphocyte activation molecules) family, is a homotypic-binding immune receptor expressed on NK, T, and B lymphocytes. The human SLAMF6 gene is transcribed into an 8-exon mRNA encoding for the SLAMF6 polypeptide. However, the existence of additional SLAMF6 isoforms (Ota et al, Nature Genetics 36, 40-45 (2004)), characterized by certain in-frame sequence deletions, has been suggested.

SLAMF6 contains two extracellular Ig-like domains and three cytoplasmic tyrosine-based signaling motifs. Engagement of SLAMF6 on human T cells can substitute the CD28 co-stimulatory pathway and induce polarization toward a Th1 phenotype. However, CD4-positive T cells from Ly-108 knockout mice (the murine SLAMF6 ortholog) show impairment in IL-4 production, suggesting a role of SLAMF6 in Th2 polarization. The reason for this discrepancy is not fully elucidated. Activation of SLAMF6 on human NK cells stimulates cytotoxicity and proliferation, as well as IFN-$\gamma$ and TNF-$\alpha$ production.

Valdez et al (J Biol Chem 2004, 279(18), pp. 18662-18669) teach that SLAMF6 activates T cells by homotypic interactions, and specifically enhances Th1 properties. US 2009/017014 to Valdez et al is directed to the PRO20080 polypeptide (having an amino acid sequence corresponding to that of canonical SLAMF6), the extracellular portion thereof, homologs, agonists and antagonists thereof, which are suggested as putative modulators of immune diseases. Uzana et al. (J Immunol 2012, 188, pp. 632-640) disclose that SLAMF6 blockade on antigen presenting cells (APC) by specific antibodies inhibited cytokine secretion from CD8$^+$ lymphocytes.

Since SLAMF6 is expressed on certain hematopoietic tumors, vaccination using peptide epitopes derived from this molecule has been proposed, to induce an anti-tumor immune response against tumors aberrantly expressing this antigen. See, e.g., WO 2006/037421. In addition, targeting these epitopes with antibodies or immunotoxin conjugates thereof has been suggested, e.g. in US2011171204.

WO 2015/104711, to some of the present inventors, discloses the use of soluble NTB-A polypeptides or agonists thereof for the treatment of cancer patients, for preventing and treating cytopenia in susceptible patients, and for the ex vivo preparation of improved T cell compositions for adoptive cell therapy. Eisenberg et al. (Cancer Immunol Res; 6(2) 2018), of some of the present inventors, further describes experiments performed using a 203-amino acid sequence of the canonical human SLAMF6 ectodomain (fused with a polyhistidine tag at the C-terminus, Novoprotein) on CD8$^+$ T-cell effector function and anti-melanoma activity.

Isoforms of murine SLAMF6 (Ly-108) have been reported and characterized (Keszei et al., J. Exp. Med. 2011, 208(4): 811-822; Wu et al., Nat Immunol. 2016, April; 17(4):387-96). The three identified Ly-108 isoforms, resulting from alternative splicing, have identical extracellular domains but differing cytoplasmic tails, due to omission of one or more of exons 7-9 (encoding inter alia for the ITSM motifs). Ly-108 isoforms were found to be associated with either susceptibility to, or protection from, lupus-related autoimmunity in mice. However, no difference in the activity of Ly-108 isoforms was found in the context of anti-tumor immunity. Rather, Wu et al. have reported that expression of different Ly-108 isoforms in NK cells resulted in enhanced responsiveness towards non-hematopoietic tumor cell lines, regardless of the transfected isoform.

Wu et al. have also reported that SLAMF6 knockout by genome editing of human NK cells resulted in decreased anti-cancer activity.

No equivalent isoforms with altered cytoplasmic tails (as detected and characterized in mice) were identified in human SLAMF6. Rather, SLAMF6 variant 2 (SLAMF6$^{var2}$) differs from canonical SLAMF6 (SLAMF6$^{var1}$) by deletion of a single alanine at position 266 (corresponding to the cytoplasmic tail), SLAMF6 variant 3 (SLAMF6$^{var3}$) lacks amino acids (aa) 17-65 of exon 2 (corresponding to the extracellular domain), and SLAMF6 variant 4 (SLAMF6$^{var4}$) lacks exon 2 and encoded aa 18-128.

Recently, the inventors and co-workers have discovered that all SLAMF6 isoforms are constitutively apparent on T-cells, regardless of their activation or differentiation state, and identified a difference in the level of isoforms transcripts in CD8$^+$ subsets in healthy donors. It was also shown that two of the isoforms were associated with opposing effects on T cell activation. Attempts at developing splice-switching oligonucleotides directed at the SLAMF6 transcript were also reported (Hajaj et al., EACR-AACR-ISCR—The Cutting Edge of Contemporary Cancer Research, 2018).

WO 2019/155474, to some of the present inventors, relates to improved therapeutic modalities for cancer immunotherapy involving specifically modulating the expression and/or activity of SLAMF6 splice variants. WO '474 discloses inter alia compositions and methods for cancer therapy, including adoptive T cell transfer therapies, cell vaccines and/or polypeptide-based medicaments. The publication further discloses compositions and methods providing selective augmentation of SLAMF6 variant 3 (SLAMF6$^{var3}$) expression or activity on T cells and/or tumor cells.

Yigit et al., (2019, Clin Immunol 204: 3-13), relates to the involvement of SLAMF6 in health and disease, and considers implications for therapeutic targeting. The publication discloses that SLAMF6 is expressed on both human and mouse chronic lymphocytic leukemia (CLL) cells, and has been implicated in B-T cell signaling, and thus it was plausible to hypothesize that monoclonal antibodies target-ing SLAMF6 may be of therapeutic interest in CLL. Yigit et al further report on experiments performed with anti-SLAMF6 antibodies in various CLL models, to explore their antibody-mediated therapeutic effects.

US 2017/334989 is directed to anti-NTB-A antibodies and antigen-binding fragments thereof, to pharmaceutical compositions comprising same, and to methods of their use to bind NTB-A and treat diseases, such as hematologic malignancies characterized by expression of NTB-A. US '989 describes in Example 9 thereof the use of certain siRNA oligonucleotides (designated SEQ ID NOs: 18 and 19 therein) to knock-down NTB-A (SLAMF6) expression in various cells, in order to demonstrate the specificity of the new antibodies. The publication demonstrates that cells that lack SLAMF6 expression, either naturally or following siRNA treatment, were resistant to complement-dependent cytotoxicity (CDC). In other words, the oligonucleotides disclosed in US '989 were demonstrated to have a negative, detrimental effect in the context of cancer therapy, as they significantly reduced the anti-cancer cytotoxic activity exerted by therapeutic antibodies.

Alternative splicing is the process by which precursor mRNAs (pre-mRNAs) are spliced differentially, leading to distinct mRNA and protein isoforms, thus increasing the diversity of the human transcriptome and proteome. Alter-native splicing is regulated by cis-acting elements within pre-mRNAs and trans-acting factors. The essential cis-acting elements are the 5' splice site, the 3' splice site, as well as the branchpoint sequence, which conform to partially conserved motifs that are recognized by cognate trans-acting factors. However additional cis-acting elements that regulate alternative splicing are known, including exonic or intronic splicing enhancers and silencers (ESEs, ISEs, ESSs, ISSs), which respectively activate or repress use of particular splice sites or exon inclusion Antisense oligonucleotides (ASOs) are synthetic mol-ecules comprised of nucleotides or nucleotide analogues that bind to a complementary sequence through Watson-Crick base-pairing. Although all ASO approaches make use of short nucleic acids that specifically base-pair to a targeted sequence, the outcome of such base-pairing depends on the chemistry of the oligonucleotide and the binding location. Splice-switching antisense oligonucleotides (SSOs) are ASOs that are typically 15-30 nucleotides long and designed to base-pair and create a steric block to the binding of splicing factors to the pre-mRNA. In this way, SSO base-pairing to a target RNA alters the recognition of splice sites by the spliceosome, which leads to an alteration of normal splicing of the targeted transcript (Havens et al., Nucleic Acids Research, 2016, Vol. 44, No. 14 6549-6563).

Nucleotides of an SSO are chemically modified so that the RNA-cleaving enzyme RNase H is not recruited to degrade the pre-mRNA-SSO complex. Thus, SSOs modify splicing without necessarily altering the abundance of the mRNA transcript. The RNAse H-resistant features of SSOs are considered important, as the goal of SSOs is to alter splicing and not to cause the degradation of the bound pre-mRNA, unlike other antisense or silencing-based approaches. Vari-ous SSO strategies have been demonstrated to be effective in modulating splicing in animal models of human disease and some have entered clinical trials, for example in the treat-ment of pediatric genetic disorders such as Duchenne Mus-cular Dystrophy and Spinal Muscular Atrophy (Havens et al., ibid).

While the development of SSO for the treatment of cancer and other diseases is desirable, identifying splice-regulating elements and regions, and designing oligonucleotides hav-ing sufficient efficacy in inducing splice switching that may be used therapeutically, remain challenging. It would also be beneficial to develop additional immune-modulating agents and therapies for enhancing the efficacy of cancer immuno-therapy.

SUMMARY OF THE INVENTION

The invention relates to nucleic acid agents modulating the expression of SLAMF6 isoforms, compositions com-prising same and methods for their use in cancer manage-ment and immunomodulation. Specifically, provided are antisense oligonucleotides (ASOs), including splice-switch-ing oligonucleotides (SSOs), nucleic acid constructs encod-ing them, and methods of using same. The invention further relates to uses of the advantageous oligonucleotides and constructs in the preparation of cell compositions for adop-tive transfer immunotherapy.

The invention is based, in part, on the discovery of antisense agents that are exceptionally effective in modify-ing the expression of SLAMF6 isoforms and improving anti-tumor immunity. Previous attempts to develop splice-switching oligonucleotides (Hajaj et al., 2018) either failed at producing molecules capable of inducing alterations in SLAMF6 isoform expression, and/or failed at demonstrating any therapeutic improvement, despite an observed modula-tion of isoform expression. Herein, the invention provides in some embodiments ASOs directed to a newly identified region within exon 2, capable of modulating the relative expression levels of SLAMF6 isoforms and enhancing T cell functionality. As demonstrated herein for the first time, treatment of human T cells with ASOs specifically hybrid-izable with target sequences as described hereinbelow, resulted in improved responsiveness to activation stimuli and in enhanced secretion of IL-2. These partly overlapping ASOs, herein identified as ASO1 and ASO2, were capable of reducing SLAMF6$^{var1}$ expression while elevating or at least retaining SLAMF6$^{var3}$ expression, and improving immune reactivity. Other partially overlapping ASOs, or ASOs directed to target sequences within the SLAMF6 pre-mRNA hitherto considered to contain splice-modulating elements, did not exert equivalent effects.

Further, the ASOs of the invention also demonstrated remarkable efficacy in an in-vivo tumor model. ASO-treated T cells were significantly more effective in reducing tumor load in a melanoma model in mice than untreated T cells, and arrested the development of tumors in these mice. The SLAMF6 splice-switching was also correlated with the formation of a transcriptional profile consistent with enhanced effector T cell functions and reduced T cell exhaustion.

Thus, the invention relates according to a first aspect to newly disclosed oligonucleotides having advantageous properties. Provided herein in some embodiments are SLAMF6 expression-modulating oligonucleotides, specifi-cally hybridizable with a nucleic acid target selected from the group consisting of SEQ ID NOs: 4, 6 or 7, as described below. In other embodiments, provided are synthetic oligo-nucleotides as set forth in any one of SEQ ID NOs: 1-2, as described below.

Without wishing to be bound by a specific theory or mechanism of action, oligonucleotides according to embodi-ments of the invention are splice-switching oligonucle-otides, which specifically hybridize with target sequences within a SLAMF6 pre-mRNA, thereby modulating SLAMF6 splicing. In some embodiments, oligonucleotides of the invention are capable of inducing or enhancing skipping of at least a part of exon 2 in a human SLAMF6 transcript.

The oligonucleotides of the invention are typically 15-30 nucleotides in length, more typically 17-23, 18-22 or 19-21 nucleotides in length, e.g. 20-mer oligonucleotides. In some embodiments, the oligonucleotides of the invention are at least 90%, at least 95% or at least 98% complementary to a nucleic acid target described herein.

Provided herein, in one embodiment, is a SLAMF6 expression-modulating oligonucleotide of 15-30 nucleotides in length, specifically hybridizable with a nucleic acid target as set forth in SEQ ID NO: 4, as follows: ATCTCTTGCCTTCATAGTACCCCATGAAA (SEQ ID NO: 4). In another embodiment, said oligonucleotide is specifically hybridizable with a nucleic acid target as set forth in SEQ ID NO: 4 and not with a nucleic acid target as set forth in SEQ ID NO: 8, as follows: CATAGTACCC-CATGAAACCA (SEQ ID NO: 8).

Exemplary ASOs specifically hybridizable with SEQ ID NO:4, demonstrated herein to encompass exceptionally beneficial properties, were identified with the following nucleic acid sequences: GGGUACUAUGAAGGCAAGAG (ASO1, SEQ ID NO: 1) and UCAUGGGGUAC-UAUGAAGGC (ASO2, SEQ ID NO: 2). The specific target sequences to which these ASOs are directed are CTCTTGCCTTCATAGTACCC and GCCTTCAT-AGTACCCCATGA (SEQ ID NOs: 6 and 7, respectively).

In another embodiment, said oligonucleotide is specifically hybridizable with a nucleic acid target as set forth in SEQ ID NO: 6 and not with a nucleic acid target as set forth in SEQ ID NO: 8. In another embodiment, said oligonucleotide is specifically hybridizable with a nucleic acid target as set forth in SEQ ID NO: 7 and not with a nucleic acid target as set forth in SEQ ID NO: 8.

In some embodiments, the invention relates to a SLAMF6 expression-modulating oligonucleotide of 15-30 nucleotides in length, specifically hybridizable with a nucleic acid target selected from the group consisting of SEQ ID NOs: 4, 6 or 7, and not with a target as set forth in SEQ ID NO: 8. In another embodiment the oligonucleotide is at least 90%, at least 95% or at least 98% complementary to the nucleic acid target. In another embodiment said oligonucleotide is 18-22 nucleotides in length. In another embodiment said oligonucleotide is specifically hybridizable with SEQ ID NO: 6 or 7. In another embodiment said oligonucleotide has the nucleic acid sequence as set forth in any one of SEQ ID NOs: 1-2. Each possibility represents a separate embodiment of the invention. As disclosed in some embodiments herein, the oligonucleotides have been demonstrated to modulate the expression of SLAMF6 isoforms in T-cells and enhance anti-tumor immunity of said cells.

Typically and conveniently, oligonucleotides of the invention intended for therapeutic use are provided as single-stranded RNA molecules. In addition, oligonucleotides of the invention, especially if intended for in vivo use, are typically derivatized by one or more backbone and/or sugar chemical modifications. In particular, oligonucleotides of the invention intended for therapeutic splice switching typically comprise one or more 2' sugar modifications, including, but not limited to, 2'-O-Methyl (2'-O-Me), 2'-O-methoxyethyl (2'-MOE), and combinations thereof. By means of a non-limitative example, said oligonucleotides may be fully derivatized by 2'-O-Me and/or 2'-MOE, e.g. may contain 2'-O-Me or 2'-MOE on each base in the sequence. For example, ASO1 and ASO2 as used in the Examples section below, correspond to SEQ ID NOs: 1 and 2, respectively, that are comprised of 2'-O-Me or 2'-MOE nucleosides, as detailed therein. Additionally or alternatively, the oligonucleotides may contain nucleic acid analogs comprising e.g. a 2'-O, 4'-C methylene bridge, such as locked nucleic acids (LNA), phosphorothiate (PS) backbone modification, phosphorodiamidate morpholinos (PMOs), and the like.

In another aspect, there is provided a nucleic acid construct encoding one or more oligonucleotides of the invention. In one embodiment, the construct is an expression vector capable of expressing said one or more oligonucleotides in mammalian cells, e.g. in human T cells (including, but not limited to viral vectors, e.g. adeno-associated virus (AAV)-based vectors). In another aspect, the invention relates to a host cell comprising a nucleic acid construct of the invention.

In other embodiments, the invention relates to a pharmaceutical composition comprising one or more therapeutic agents as disclosed herein, e.g. an oligonucleotide, a construct or a host cell as described herein, and optionally a pharmaceutically acceptable carrier, excipient or diluent.

The pharmaceutical composition may be used therapeutically, e.g. in cancer management. For example, the invention relates in some embodiments to said pharmaceutical composition for use in the treatment of cancer, or in inducing or enhancing anti-tumor immunity. In another embodiment, said composition may be used for inducing or enhancing splice switching in vitro.

In another aspect, the invention relates to a method of treating cancer in a subject in need thereof, comprising administering to the subject, or expressing in cells of said subject, one or more SLAMF6 expression-modulating oligonucleotides of the invention. Typically, said method comprises administering to said subject a pharmaceutical composition as disclosed herein. For example, the pharmaceutical composition may comprise an effective amount of one or more oligonucleotides of 15-30 nucleotides in length specifically hybridizable with a nucleic acid target as set forth in SEQ ID NO: 4, e.g. a synthetic oligonucleotide as set forth in any one of SEQ ID NOs: 1 and 2, which may be derivatized by one or more 2' sugar modifications.

Typically, the subjects to be treated by the methods of the invention are afflicted with solid tumors. It is to be understood, that subjects afflicted with hematologic malignancies in which the tumor cells are lymphocytes or other SLAMF6-expressing cells, are excluded from currently preferred embodiments of the invention in which in vivo administration of synthetic oligonucleotides as described herein is contemplated. However, in some embodiments, for example when ex-vivo modulation of cells and re-administration is employed (e.g. in ACT protocols), the treatment of hematologic malignancies is further contemplated.

In various embodiments, the cancer may be melanoma, renal cell carcinoma, lung cancer, breast cancer, or head and neck cancer. In other embodiments, the cancer may be e.g. melanoma, urinary tract cancer, gynecological cancer, head and neck carcinoma, primary brain tumor, bladder cancer, liver cancer, lung cancer, breast cancer, ovarian cancer, prostate cancer, cervical cancer, colon cancer and other cancers of the intestinal tract, bone malignancies, connective and soft tissue tumors, or skin cancers. In a particular embodiment, said cancer is melanoma. In another embodiment the subject is further treated by a cancer immunotherapy. In a particular embodiment the cancer immunotherapy is a T-cell mediated immunotherapy.

In another aspect, there is provided a method of inducing or enhancing anti-tumor immunity in a subject in need thereof, comprising administering to the subject, or expressing in cells of the subject, one or more SLAMF6 expression-modulating oligonucleotides of the invention.

In another aspect, there is provided a method of inducing or enhancing splice switching in SLAMF6 expressing cells, comprising administering to, or expressing in the cells, one or more SLAMF6 expression-modulating oligonucleotides of the invention. In one embodiment, said cells are T cells. In another embodiment, said method is performed in vitro. In another embodiment, said method is performed in vivo.

In another aspect there is provided a method for preparing a T cell composition adapted for adoptive transfer immunotherapy, comprising the step of administering to, or expressing in, a T cell population, one or more SLAMF6 expression-modulating oligonucleotides of the invention, in an amount and under conditions suitable for inducing or enhancing splice switching in the cell population.

In one embodiment, the method comprises:
- a. providing a T cell population comprising CD8+ T cells,
- b. administering to, or expressing in the T cell population, one or more SLAMF6 expression-modulating oligonucleotides of the invention, in an amount and under conditions suitable for inducing or enhancing splice switching in said T cell population,
- c. expanding said T cell population, so as to obtain a T cell composition adapted for adoptive transfer immunotherapy comprising an effective amount of the resulting T cell population.

In another embodiment, step c is performed by a rapid expansion protocol (REP). In another embodiment, step c is performed by providing said cell population with a TCR stimulation and at least one co-stimulation. In another embodiment, step c is performed by providing said cell population with a TCR stimulation and a SLAMF6-mediated stimulation. In another embodiment, said cell population (e.g. as provided in step a) is selected from the group consisting of tumor infiltrating leukocytes (TIL), tumor-specific T cell clones, and genetically modified T cells. In another embodiment said cell population expresses a chimeric antigen receptor (CAR). In another embodiment, step b may be performed by methods known in the art, for example the oligonucleotides may be administered to the cells e.g. by electroporation, using Nucleofector technology, (AMAXA), or by other transfection methods e.g. liposome-mediated transfer. The oligonucleotides may also be expressed in the cells following transfection or infection with a suitable construct (including, but not limited to viral vectors, e.g. AAV-based vectors) encoding the oligonucleotides. In another embodiment, step c is performed prior to step b.

In another aspect the invention relates to a T cell composition adapted for adoptive transfer immunotherapy prepared by the method disclosed herein. In another aspect the invention relates to a T cell composition adapted for adoptive transfer immunotherapy prepared by the method disclosed herein, for use in the treatment of cancer, or in inducing or enhancing anti-tumor immunity. In another embodiment, the tumor is a solid tumor.

According to certain embodiments, provided are SLAMF6 expression-modulating oligonucleotides, specifically hybridizable with a nucleic acid target selected from the group consisting of SEQ ID NOs: 4-8, as described below, wherein each possibility represents a separate embodiment of the invention. In other embodiments, provided are synthetic oligonucleotides as set forth in any one of SEQ ID NOs: 1-3, as described below, wherein each possibility represents a separate embodiment of the invention. In another embodiment said oligonucleotide is a single-stranded RNA molecule. In another embodiment, said oligonucleotide is derivatized by one or more 2' sugar modifications. In a particular embodiment, said oligonucleotide is as set forth in SEQ ID NO:1, fully derivatized by 2'-O-Me or 2'-MOE. In another particular embodiment, said oligonucleotide is as set forth in SEQ ID NO:2, fully derivatized by 2'-O-Me or 2'-MOE. In another particular embodiment, said oligonucleotide is as set forth in SEQ ID NO:3, fully derivatized by 2'-O-Me or 2'-MOE. Additional oligonucleotides useful for certain applications are described in the Examples section below.

Other objects, features and advantages of the present invention will become clear from the following description and drawings.

BRIEF DESCRIPTION OF THE DRAWINGS

FIG. 8A—Tox; FIG. 8B—Eomes; FIG. 8C—c-jun; FIG. 8D—Runx3; FIG. 8E—Tcf7; FIG. 8F—Tbet; FIG. 8G—Bcl6; FIG. 8H—Id2; FIG. 8I—Gata3.

DETAILED DESCRIPTION OF THE INVENTION

Figures 1A, 1B:
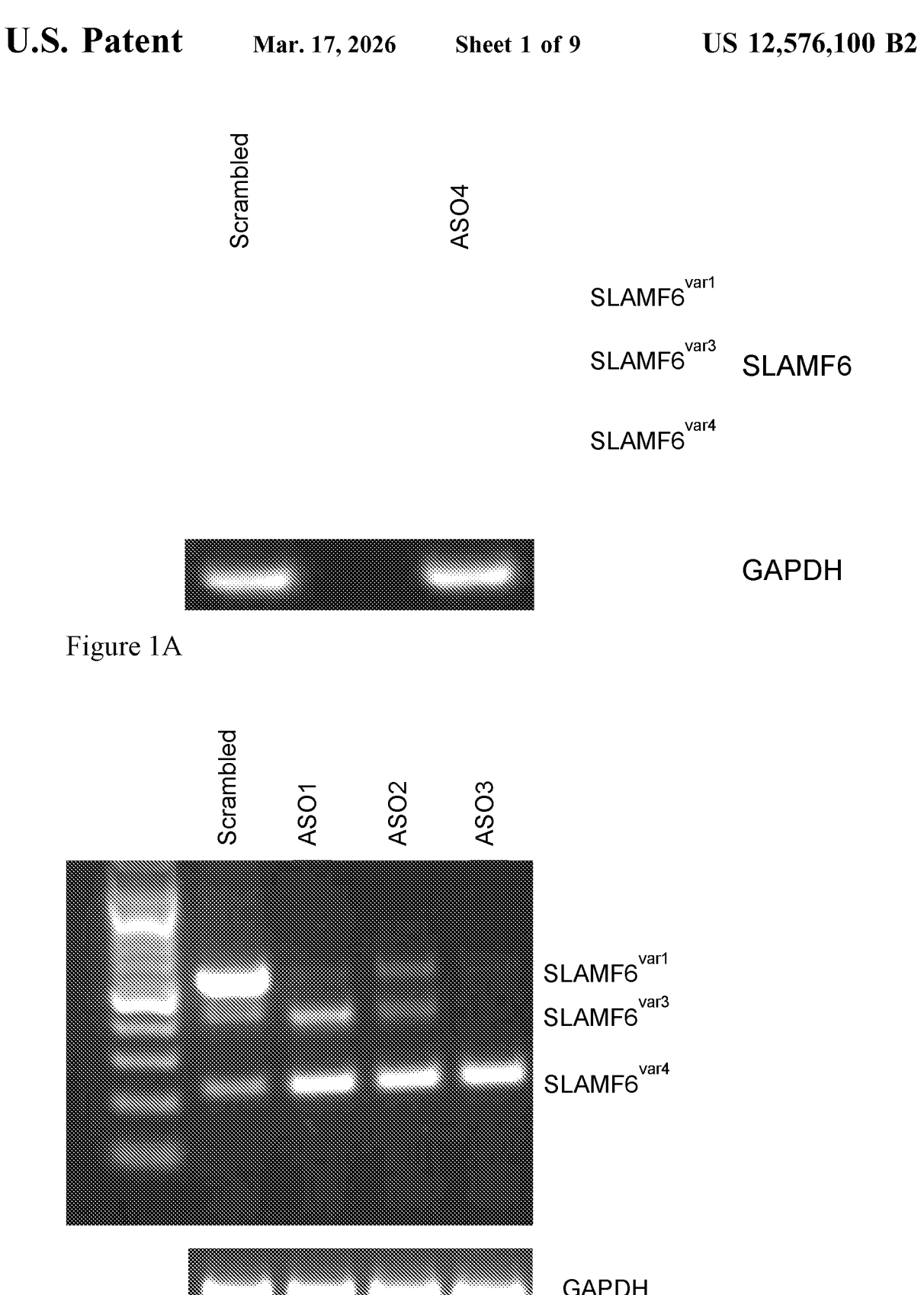
FIG. 1A presents the expression pattern of SLAMF6 isoforms in Jurkat cells following treatment with ASO4 or a control ASO (scrambled).
FIG. 1B presents the expression patterns of SLAMF6 isoforms in Jurkat cells following treatment with ASO1-ASO3 or control ASO.

The invention relates to nucleic acid agents modulating the expression of SLAMF6 isoforms, compositions comprising same and methods for their use in cancer management and immunomodulation. Specifically, provided are antisense oligonucleotides (ASOs), including splice-switching oligonucleotides (SSOs), nucleic acid constructs encoding them, and methods of using same. The invention further relates to uses of the advantageous oligonucleotides and constructs in the preparation of cell compositions for adoptive transfer immunotherapy.

The invention is based, in part, on the identification of splice-switching oligonucleotides, capable of augmenting anti-tumor immunity and arresting tumor formation in vivo. It is noted, that hitherto described oligonucleotides, for example isoform non-specific siRNAs directed to SLAMF6 as disclosed by US 2017/334989, were not suitable for use as anti-cancer agents; such oligonucleotides are also incapable of enhancing the expression of SLAMF6 isoforms, as do splice-switching oligonucleotides.

In addition, previous attempts to develop splice-switching oligonucleotides either failed at producing molecules capable of inducing alterations in SLAMF6 isoform expression, and/or failed at demonstrating any therapeutic improvement, despite an observed modulation of isoform expression. In contradistinction, the invention discloses, for the first time, short oligonucleotides (15-30 na long), that are capable of enhancing the ratio of SLAMF6$^{var3}$ to SLAMF6$^{var1}$ splice transcripts in tumor-reactive T cells and exerting anti-tumor activity in vivo. Surprisingly, even though these oligonucleotides are located only several nucleotides apart from other known sequences, they manifest dramatically different and even opposing therapeutic effects in the contest of tumor management, compared to control sequences e.g. located within exon 2.

In one aspect, there is provided a SLAMF6 expression-modulating oligonucleotide of 15-30 nucleotides in length, specifically hybridizable with a nucleic acid target selected from the group consisting of ATCTCTTGCCTTCATAGTACCCCATGAAA (SEQ ID NO: 4), CTCTTGCCTTCATAGTACCC (SEQ ID NO: 6), and GCCTTCATAGTACCCCATGA (SEQ ID NO: 7), and not with the target CATAGTACCCCATGAAACCA (SEQ ID NO: 8).

In another aspect, there is provided a nucleic acid construct encoding the oligonucleotide. In another aspect there is provided a host cell comprising the construct. In another aspect, there is provided a pharmaceutical composition comprising the oligonucleotide, construct or host cell, and optionally a pharmaceutically acceptable carrier, excipient or diluent. In another aspect, the pharmaceutical is for use in the treatment of cancer. In another aspect, said pharmaceutical is for use in inducing or enhancing anti-tumor immunity.

In another aspect, there is provided a method for preparing a T cell composition adapted for adoptive transfer immunotherapy, comprising the step of administering to, or expressing in, a T cell population, an oligonucleotide of the invention, in an amount and under conditions suitable for inducing or enhancing splice switching in the T cell population. In one embodiment, the method comprises:
- a. providing a T cell population comprising CD8$^+$ T cells,
- b. administering to, or expressing in the T cell population, one or more SLAMF6 expression-modulating oligonucleotides of the invention, in an amount and under conditions suitable for inducing or enhancing splice switching in said T cell population, and
- c. expanding said T cell population, so as to obtain a T cell composition adapted for adoptive transfer immunotherapy comprising an effective amount of the resulting T cell population.

In another aspect, there is provided a T cell composition adapted for adoptive transfer immunotherapy prepared by the method. In another aspect, the T cell composition is for use in the treatment of cancer. In another aspect, said T cell composition is for use in inducing or enhancing anti-tumor immunity.

In other embodiments, there are provided synthetic oligonucleotides selected from the group consisting of GGGUACUAUGAAGGCAAGAG, UCAUGGGGUACUAUGAAGGC and UGGUUUCAUGGGGUACUAUG (SEQ ID NOs: 1-3, respectively), wherein each possibility represents a separate embodiment of the invention.

SLAMF6 Variants

Generally, SLAMF6 is comprised of the following domains in the order of N' to C':
- I. an N-terminal signal peptide;
- II. an extracellular portion (ectodomain), comprising two conserved immunoglobulin (Ig)-like motifs: an N' Ig-like V-type domain (IgV, having a two-layered β-sheet structure, with predominantly neutral, albeit polar, front surfaces), and a C' Ig-like C2-type domain (IgC2, characterized by an overall β-strand topology and several disulfide bonds);
- III. a helical transmembrane domain; and
- IV. a topological (cytoplasmic) domain, containing immunoreceptor tyrosine-based switch motifs (ITSMs), which are docking sites for the SH2 domain of SLAM-associated protein (SAP) and the related Ewing's sarcoma-associated transcript. ITSM motifs carry the consensus sequence TxYxxV/I/L that have overlapping specificity for activating and inhibitory binding partners.

In canonical human SLAMF6 (e.g. accession no. Q96DU3, isoform 1), the signal peptide has been identified to be located at positions 1-21 of the transcribed polypeptide, the ectodomain has been identified to be located at positions 22-226 (wherein IgV was located at positions 35-120 and IgC2 at positions 132-209), the transmembrane domain was located at positions 227-247, and the cytoplasmic (intracellular) domain—at positions 248-331. Exon 2 encodes for the amino acids at positions 17-128.

The amino acid sequence of human SLAMF6$^{var1}$ (precursor, also provided in accession no. NM_001184714.1), is as follows:

```
                                  (SEQ ID NO: 13)
MLWLFQSLLFVFCFGPGNVVSQSSLTPLMVNGILGESVTLPLEFPAGEKV

NFITWLFNETSLAFIVPHETKSPEIHVTNPKQGKRLNFTQSYSLQLSNLK

MEDTGSYRAQISTKTSAKLSSYTLRILRQLRNIQVTNHSQLFQNMTCELH

LTCSVEDADDNVSFRWEALGNTLSSQPNLTVSWDPRISSEQDYTCIAENA

VSNLSFSVSAQKLCEDVKIQYTDTKMILFMVSGICIVFGFIILLLLVLRK

RRDSLSLSTQRTQGPAESARNLEYVSVSPTNNTVYASVTHSNRETEIWTP

RENDTITIYSTINHSKESKPTFSRATALDNVV.
```

Human SLAMF6$^{var2}$ differs from SLAMF6$^{var1}$ by deletion of a single alanine at position 266 relative to SEQ ID NO: 13.

Human SLAMF6$^{var3}$ (precursor, NM_001184715.1) differs from SLAMF6$^{var1}$ by deletion of amino acids (aa) 17-65 relative to SEQ ID NO: 13. The deletion includes aa 17-21 residing in the signal peptide, and aa 22-65, residing in the ectodomain. The precursor sequence denoted by accession number NM_001184715.1 is as follows:

(SEQ ID NO: 14)

MLWLFQSLLFVFCFGPVPHETKSPEIHVTNPKQGKRLNFTQSYSLQLSNL

KMEDTGSYRAQISTKTSAKLSSYTLRILRQLRNIQVTNHSQLFQNMTCEL

HLTCSVEDADDNVSFRWEALGNTLSSQPNLTVSWDPRISSEQDYTCIAEN

AVSNLSFSVSAQKLCEDVKIQYTDTKMILFMVSGICIVFGFIILLLLVLR

KRRDSLSLSTQRTQGPESARNLEYVSVSPTNNTVYASVTHSNRETEIWTP

RENDTITIYSTINHSKESKPTFSRATALDNV,

Human SLAMF6$^{var4}$ (precursor, NM_001184716.1) differs from SLAMF6$^{var1}$ by deletion of aa 18-128 relative to SEQ ID NO: 13.

Nucleic Acid Agents

The nucleic acid agents designed according to the teachings of the present invention can be generated according to any nucleic acid synthesis method known in the art, including both enzymatic syntheses or solid-phase syntheses, as well as using recombinant methods well known in the art.

Equipment and reagents for executing solid-phase synthesis are commercially available from, for example, Applied Biosystems. Any other means for such synthesis may also be employed; the actual synthesis of the nucleic acid agents is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Maryland; Perbal, B. (1988), "A Practical Guide to Molecular Cloning," John Wiley & Sons, New York; utilizing solid-phase chemistry, e.g. cyanoethyl phosphoramidite followed by deprotection, desalting, and purification by, for example, an automated trityl-on method or HPLC.

It will be appreciated that nucleic acid agents of the present invention can be also generated using an expression vector as is further described herein.

The oligonucleotides of the invention are typically derivatized by one or more backbone and/or sugar chemical modifications. For example, ASOs of the invention intended for inducing splice-switching in vivo advantageously contain modifications conferring resistance to nuclease-induced enzymatic degradation, and in particular to RNase H, that may degrade the pre-mRNA-ASO complex. Advantageously, oligonucleotides according to embodiments of the invention contain one or more 2' sugar modifications. For example, said modifications may advantageously be selected from the group consisting of 2'-O-Methyl (2'-O-Me), 2'-O-methoxyethyl (2'-MOE), and combinations thereof. Additionally or alternatively, the modifications may contain nucleic acid analogs comprising e.g. a 2'-O, 4'-C methylene bridge, such as locked nucleic acids (LNA). Additionally or alternatively, oligonucleotides of embodiments of the invention may also contain phosphorothiate (PS) backbone modification, phosphorodiamidate morpholinos (PMOs), and/or other modifications that may provide improved in vivo properties such as stability, tolerability, and bio-distribution.

As used herein, "uniformly modified" or "fully modified" refers to an antisense oligonucleotide, or a region of nucleotides wherein essentially each nucleoside is a sugar modified nucleoside having uniform modification.

As used herein, a "nucleoside" is a base-sugar combination and "nucleotides" are nucleosides that further include a phosphate group covalently linked to the sugar portion of the nucleoside.

As used herein, a nucleoside with a modified sugar residue is any nucleoside wherein the ribose sugar of the nucleoside has been substituted with a chemically modified sugar moiety. In the context of the present disclosure, the chemically modified sugar moieties include, but are not limited to, 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

Modified oligonucleotide backbones may include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and CH2 component parts.

Other nucleic acid agents which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone.

Nucleic acid agents of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), pages 858-859; Englisch et al. (1991); and Sanghvi (1993). Such modified bases are particularly useful for increasing the binding affinity of the oligonucleotides of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C., and may be advantageous even more particularly when combined with 2'-O-methoxyethyl sugar modifications.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, New York, 1989. The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SOS. Hybridization is carried out at about 68° C. for about 3 to 4 hours for fragments of cloned DNA and for about 12 to about 16 hours for total eukaryotic DNA. For lower stringencies the temperature of hybridization is reduced to about 42° C. below the melting temperature (TM) of the duplex. The TM is known to be a function of the G-C content and duplex length as well as the ionic strength of the solution.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the antisense oligonucleotides of the present disclosure, the binding free energy for an antisense oligonucleotide with its complementary sequence is sufficient to allow the relevant function of the antisense oligonucleotide to proceed and there is a sufficient degree of complementarity to avoid non-specific binding of the antisense oligonucleotide to non-target sequences under conditions in which specific binding is desired, i.e., under physiological conditions in the case of ex vivo or in vivo therapeutic treatment. Determination of binding free energies for nucleic acid molecules is well known in the art. Thus, "complementary" (or "specifically hybridizable") are terms that indicate a sufficient degree of complementarity or precise pairing such that stable and specific binding occurs between an antisense oligonucleotide and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. Percent complementarity of an oligonucleotide with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

Thus, in the context of the present disclosure, an oligonucleotide specifically hybridizable with a nucleic acid target as set forth herein is sufficiently complementary to its designated target such that, upon administration to a SLAMF6 expressing cell under physiological conditions, will bind to its target and not to other sequences within the cell's transcriptome. For example, the invention relates in advantageous embodiments thereof to SLAMF6 expression-modulating oligonucleotides of 15-30 nucleotides in length, that are specifically hybridizable with a nucleic acid target selected from the group consisting of SEQ ID NOs: 4, 6 or 7, and not with a target as set forth in SEQ ID NO: 8. Thus, the oligonucleotide in question is sufficiently complementary to its designated target (SEQ ID NOs: 4, 6 or 7) such that, upon administration to a SLAMF6 expressing cell under physiological conditions, will bind to its target and not to other sequences within the cell's transcriptome, such as to SEQ ID NO: 8, as demonstrated herein.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is completely devoid of intron sequences. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" and "(pre-)mRNA processing" refer to the modification of a pre-mRNA following transcription, in which introns are removed and exons are joined. Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS), exonic silencer sequences (ESS) and terminal stem loop (TSL) sequences. In other embodiments, splicing may be regulated by intronic enhancers (IES) and exonic enhancers (EES).

As used herein, "modulation of splicing" or "splice switching" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

In some embodiments, the invention relates to a SLAMF6 expression-modulating oligonucleotide of 15-30 nucleotides in length, specifically hybridizable with a nucleic acid target selected from the group consisting of SEQ ID NOs: 4, 6 or 7, and not with a target as set forth in SEQ ID NO: 8. In another embodiment the oligonucleotide is at least 90%, at least 95% or at least 98% complementary to the nucleic acid target. In another embodiment said oligonucleotide is 18-22 nucleotides in length. In another embodiment said oligonucleotide is specifically hybridizable with SEQ ID NO: 6 or 7. In another embodiment said oligonucleotide has the nucleic acid sequence as set forth in any one of SEQ ID NOs: 1-2, as follows: GGGUACUAUGAAGGCAAGAG (SEQ ID NO: 1), and UCAUGGGGUACUAUGAAGGC (SEQ ID NO: 2). Each possibility represents a separate embodiment of the invention.

In another embodiment said oligonucleotide is a single-stranded RNA molecule. In another embodiment said oligonucleotide is derivatized by one or more backbone and/or sugar chemical modifications. In another embodiment said oligonucleotide comprises one or more 2' sugar modifications. In another embodiment said modifications are selected from the group consisting of 2'-O-Methyl (2'-O-Me), 2'-O-methoxyethyl (2'-MOE), and combinations thereof, wherein each possibility represents a separate embodiment of the invention. In another embodiment said oligonucleotide is fully derivatized by 2'-O-Me or 2'-MOE. In a particular embodiment, the oligonucleotide is selected from the group consisting of SEQ ID NOs: 1 and 2 and is fully derivatized by 2'-O-Me or 2'-MOE.

As disclosed herein the oligonucleotide is typically a splice-switching oligonucleotide.

In another embodiment there is provided a nucleic acid construct encoding a SLAMF6 expression-modulating oligonucleotide of 15-30 nucleotides in length, specifically hybridizable with a nucleic acid target selected from the group consisting of SEQ ID NOs: 4, 6 or 7, and not with a target as set forth in SEQ ID NO: 8. In another embodiment there is provided a nucleic acid construct encoding an oligonucleotide as disclosed herein. In another embodiment the construct is an expression vector capable of expressing said oligonucleotide in human T cells. In another embodiment there is provided a host cell comprising the construct.

The term "construct" as used herein includes a nucleic acid sequence encoding silencing oligonucleic acid according to the present invention, the nucleic acid sequence being operably linked to a promoter and optionally other transcription regulation sequences.

The phrase "operably linked" refers to linking a nucleic acid sequence to a transcription control sequence in a manner such that the molecule is able to be expressed when transfected (i.e., transformed, transduced, infected or transfected) into a host cell. Transcription control sequences are sequences, which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Exemplary suitable transcription control sequences include those that function in animal, bacteria, helminth, yeast and insect cells. The constructs of the invention comprise mammalian transcription control sequences, preferably human regulatory sequences, and, optionally and additionally, other regulatory sequences.

The nucleic acid construct of methods and compositions of the present invention is, in another embodiment, a eukaryotic expression vector. In another embodiment, the nucleic acid construct is a plasmid. In another embodiment, the nucleic acid construct is any other type of expression vector capable of mediating expression in a cancer cell. Each possibility represents a separate embodiment of the present invention.

The construct may also comprise other regulatory sequences or selectable markers, as known in the art. Other than containing the necessary elements for the transcription of the inserted coding sequence, the expression construct of the present invention can also include sequences engineered to enhance stability, production, purification, yield or toxicity of the expressed oligonucleotide.

Various suitable prokaryotic and eukaryotic host cells with suitable expression vectors are known in the art, including, but not limited to animal cells (including mammalian cells, e.g. human cells Chinese hamster ovary cells (CHO) or COS cells), bacterial cells, plant cells, yeast cells and insect cells. According to certain advantageous embodiments, the host cell is a human cell, e.g. a T cell population as disclosed herein. For example, the host cell may be e.g. human T cells including, but not limited to tumor infiltrating leukocytes (TIL), tumor-specific T cell clones, and genetically modified T cells. In another embodiment, said host cell is a T cell containing population expresses a chimeric antigen receptor (CAR). In another specific embodiment said host cell is a T cell composition adapted for adoptive transfer immunotherapy as disclosed herein.

As demonstrated herein, nucleic acid agents of the invention are useful for SLAMF6 isoform modulation associated with improved functional capacity. In some embodiments, the oligonucleotides of the invention are splice-switching oligonucleotides, which modulate the expression of SLAMF6 isoforms in T-cells and enhance anti-cancer functions of said cells, as disclosed and exemplified herein. Specific methods for measuring anti-cancer functions such as the anti-tumor immunity of said cells (e.g. in PBMC, TIL or T cell clones), including, but not limited to, tumor-specific proliferation, lytic degranulation and/or cytokine (e.g. IL-2 or IFN-γ) secretion, are disclosed and exemplified herein. In some embodiments, said parameters are enhanced by at least 1.5-fold and advantageously by at least about 2, 3, 4 or 6-fold, e.g. by 1.5-10 folds, 2-8 folds, 1.5-6 folds, 2-6 folds or 2-4 folds. Each possibility represents a separate embodiment of the invention.

Other examples for evaluating functional capacity include modulated expression of genes associated with effector T cell function, for example up-regulation of Runx3, C-jun, and/or Tbet, and/or down-regulation of TOX, e.g. by at least 1.5-fold and typically about 2-6 folds, as demonstrated herein, wherein each possibility represents a separate embodiment of the invention. In other embodiments, functional capacity such as anti-tumor activity may be measured in vivo. For example, ASOs of the invention were demonstrated to inhibit tumor formation and exhibited at least a twofold reduction in tumor volume, e.g. by about 2-10 folds, 2-8 folds, 1.5-6 folds, 2-6 folds or 2-4 folds. In a particular embodiment, ASOs of the invention induce an enhancement of at least 1.5-fold and typically about twofold in Tbet expression (e.g. 1.7-fold). In another particular embodiment, ASOs of the invention induce an enhancement of at least 1.5-fold and typically about twofold in Runx3 expression. In another particular embodiment ASOs of the invention are capable of eliciting an enhancement of 2-6 folds in IFN-γ secretion upon stimulation in the presence of cognate tumor cells. In yet another particular embodiment are capable of eliciting an enhancement of at least 1.5-fold and typically 2-6 folds in IFN-γ secretion, Tbet expression and/or Runx3 expression upon stimulation in the presence of cognate tumor cells. Each possibility represents a separate embodiment of the invention.

In another embodiment, ASOs of the invention induce splice-switching in the cells within 12 hours of administration to said cells and up to at least 5 or 7 days thereafter. In another embodiment, ASOs of the invention are capable of enhancing the ratio of the SLAMF6$^{var3}$ to SLAMF6$^{var1}$ splice transcripts in T cells by 1.5-3.5 folds, e.g. by about twofold. In another embodiment, ASOs of the invention are capable of enhancing the ratio of the SLAMF6$^{var3}$ to SLAMF6$^{var1}$ splice transcripts in T cells by 1.5-3.5 folds, e.g. by about twofold within 12 hours of administration and up to at least 5 or 7 days thereafter. In another embodiment, ASOs of the invention are capable of enhancing the level of the SLAMF6$^{var3}$ splice transcript in T cells (e.g. by at least about 1.5-fold, 2-fold or 3-fold). Each possibility represents a separate embodiment of the invention.

According to other embodiments, the nucleic acid agents, such as the oligonucleotides and constructs described herein, or the host cells encoding them, are formulated in the form of a pharmaceutical composition, optionally further comprising a pharmaceutically acceptable carrier, excipient or diluent, as detailed below.

Pharmaceutical Compositions

Pharmaceutical compositions comprising the antisense compounds described herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleotides that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. For example, sodium salts of antisense oligonucleotides are useful and are well accepted for therapeutic administration to humans.

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated. In a particular embodiment, administration is intramuscular or intravenous.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a particular embodiment, the pharmaceutical formulations are prepared for intramuscular administration in an appropriate solvent, e.g., water or normal saline, possibly in a sterile formulation, with carriers or other agents.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

The antisense oligonucleotides described herein may be in admixture with excipients suitable for the manufacture of aqueous suspensions. Such excipients are suspending agents, for example polyvinylpyrrolidone, sodium carboxymethylcellulose, methylcellulose, hydropropyl-methylcellulose, sodium alginate, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives. Antisense oligonucleotide compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes ASO compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences (Mack Publishing Co., A.R. Gennaro edit., 1985). For example, preservatives and stabilizers can be provided. These include sodium benzoate, sorbic acid and esters of p-hydroxybenzoic acid. In addition, antioxidants and suspending agents can be used.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxy ethylene sorbitan monooleate.

The ASO of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus, the ASO of the present disclosure may be administered in any form, for example intramuscular or by local, systemic, or intrathecal injection.

This disclosure also features the use of ASO compositions comprising surface-modified liposomes containing poly (ethylene glycol) lipids (PEG-modified, or long-circulating liposomes or stealth liposomes). These formulations offer a method for increasing the accumulation of ASO in target tissues. This class of drug carriers resists opsonization and elimination by the mononuclear phagocytic system (MPS or RES), thereby enabling longer blood circulation times and enhanced tissue exposure for the encapsulated ASO. Long-circulating liposomes enhance the pharmacokinetics and pharmacodynamics of ASO, particularly compared to conventional cationic liposomes which are known to accumulate in tissues of the MPS (PCT Publication No. WO 96/10391; WO 96/10390; and WO 96/10392). Long-circulating liposomes are also likely to protect ASO from nuclease degradation to a greater extent compared to cationic liposomes, based on their ability to avoid accumulation in metabolically aggressive MPS tissues such as the liver and spleen.

Typical dosage amounts of antisense oligonucleotide molecules in pharmaceutical formulations may range from about 0.05 to 1000 mg/kg body weight, and in particular from about 5 to 500 mg/kg body weight. In one embodiment of the invention and/or embodiments thereof, the dosage amount is from about 50 to 300 mg/kg body weight once in 2 weeks, or once or twice a week, or any frequency required to achieve therapeutic effect.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment of the invention and/or embodiments thereof, dosage forms (compositions) of the inventive pharmaceutical composition may contain about 1 microgram to 50,000 micrograms of active ingredient per unit, and in particular, from about 10 to 10,000 micrograms of active ingredient per unit. For intravenous delivery, a unit dose of the pharmaceutical formulation will generally contain from 0.5 to 500 micrograms per kg body weight and preferably will contain from 5 to 300 micrograms, in particular 10, 15, 20, 30, 40, 50, 100, 200, or 300 micrograms per kg body weight ($\mu$g/kg body weight) of the antisense oligonucleotide molecule. Preferred intravenous dosage ranges from 10 ng to 2000 $\mu$g, preferably 3 to 300 $\mu$g, more preferably 10 to 100 $\mu$g of compound per kg of body weight.

In one particular embodiment, it should be recognized that the dosage can be raised or lowered based on individual patient response. It will be appreciated that the actual amounts of antisense oligonucleotide molecule used will vary according to the specific antisense oligonucleotide molecule being utilized, the particular compositions formulated, the mode of application, and the particular site of administration.

In a particular embodiment, antisense oligonucleotides of the invention may be delivered in vivo alone or in association with a vector (expression vector or delivery vector). In its broadest sense, a "vector" is any vehicle (e.g. nucleic acid construct as disclosed herein) capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non-viral delivery systems (electroporation, sonoporation, cationic transfection agents, liposomes, etc.), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: RNA or DNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Preferred viral vectors according to the invention include adenoviruses and adeno-associated (AAV) viruses, which are DNA viruses that have already been approved for human use in gene therapy. 12 different AAV serotypes (AAV1 to 12) are known, each with different tissue tropisms. Recombinant AAV are derived from the dependent parvovirus AAV. The adeno-associated virus type 1 to 12 can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al, 1989. They are particularly advantageous for this because they do not have the same safety concerns as with many of the viral vectors. These plasmids, however, having a promoter compatible with the host cell, can express a gene product from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected intramuscular, or intravenous. It may also be administered into the epidermis or a mucosal surface using a gene-gun. The plasmids may be given in an aqueous solution, dried onto gold particles or in association with another DNA delivery system including but not limited to liposomes, dendrimers, cochleates and micro-encapsulation.

In a preferred embodiment of the invention and/or embodiments thereof, the antisense oligonucleotide nucleic acid sequence is under the control of a heterologous regulatory region, e.g., a heterologous promoter. The promoter can also be, e.g., a viral promoter, such as CMV promoter or any synthetic promoters. In another embodiment of the invention and/or embodiments thereof, the vector may code for more than one ASO.

In some embodiments, there is provided a pharmaceutical composition comprising a nucleic acid construct encoding an oligonucleotide as disclosed herein, e.g. an expression vector capable of expressing said oligonucleotide in human T cells. In other embodiments there is provided a pharmaceutical composition comprising an oligonucleotide as disclosed herein. In other embodiments there is provided a pharmaceutical composition comprising a host cell as disclosed herein (e.g. a population of human T cells including, but not limited to an adoptive transfer cell composition as disclosed herein).

Subjects and Methods

In various embodiments, the invention relates to compositions and methods for the treatment of cancer, for inducing or enhancing anti-tumor immunity and/or for inducing or enhancing splice switching, wherein each possibility represents a separate embodiment of the invention.

In another embodiment there is provided a pharmaceutical composition comprising the oligonucleotide, construct or host cell as disclosed herein, and optionally a pharmaceutically acceptable carrier, excipient or diluent, for use in the treatment of cancer, for inducing or enhancing anti-tumor immunity and/or for inducing or enhancing splice switching, wherein each possibility represents a separate embodiment of the invention.

In another embodiment there is provided a method of treating cancer in a subject in need thereof, comprising administering to the subject, or expressing in cells of said subject, one or more SLAMF6 expression-modulating oligonucleotides of 15-30 nucleotides in length, wherein each oligonucleotide is specifically hybridizable with a nucleic acid target selected from the group consisting of SEQ ID NOs: 4, 6 or 7, and not with a target as set forth in SEQ ID NO: 8.

In another embodiment there is provided a method of inducing or enhancing anti-tumor immunity in a subject in need thereof, comprising administering to the subject, or expressing in cells of the subject, one or more SLAMF6 expression-modulating oligonucleotides of 15-30 nucleotides in length, wherein each oligonucleotide is specifically hybridizable with a nucleic acid target selected from the group consisting of SEQ ID NOs: 4, 6 or 7, and not with a target as set forth in SEQ ID NO: 8.

In another embodiment there is provided a method of inducing or enhancing splice switching in SLAMF6 expressing cells, comprising administering to, or expressing in the cells, one or more SLAMF6 expression-modulating oligonucleotides of 15-30 nucleotides in length, wherein each oligonucleotide is specifically hybridizable with a nucleic acid target selected from the group consisting of SEQ ID NOs: 4, 6 or 7, and not with a target as set forth in SEQ ID NO: 8. In another embodiment said cells are T cells. In another embodiment said method is performed in vitro. In another embodiment said method is performed in vivo.

In some embodiments, the subjects to be treated by the compositions and methods of the invention is afflicted with cancer, or at risk for developing cancer (e.g. afflicted with a pre-cancerous lesion or diagnosed with a condition associated with high risk for tumor formation). In another embodiment said subject has been diagnosed with cancer. Advantageously, said subject is a human subject.

In another embodiment, the cancer is a solid tumor. In various embodiments, the cancer is selected from the group consisting of melanoma, renal cell carcinoma, lung cancer, breast cancer, and head and neck cancer, wherein each possibility represents a separate embodiment of the invention. In other embodiments, the cancer may be e.g. melanoma, urinary tract cancer, gynecological cancer, head and neck carcinoma, primary brain tumor, bladder cancer, liver cancer, lung cancer, breast cancer, ovarian cancer, prostate cancer, cervical cancer, colon cancer and other cancers of the intestinal tract, bone malignancies, connective and soft tissue tumors, or skin cancers. In a particular embodiment, said cancer is melanoma. In another embodiment the cancer is metastatic. In another embodiment the compositions and methods are used for preventing or delaying the formation of tumor metastasis.

In another embodiment the subject is further treated by a cancer immunotherapy. In another embodiment the method further comprises administering to the subject a cancer immunotherapy. In a particular embodiment the cancer immunotherapy is a T-cell mediated immunotherapy (directed at inducing, enhancing or otherwise modulating the activity of T cells in the subject). For example, without limitation, the immunotherapy may involve the use of immune checkpoint inhibitors (e.g. anti-PD1, anti-PDL1, anti-CTLA4, anti-Lag3, anti-Tim3, anti-Tigit, anti-41BB, anti-GITR, and/or anti-OX40 antibodies or inhibitors), CTL stimulators (e.g. anti-CD40 antibodies or agonists thereof), cytokines (e.g. IL-2), or combined with adoptive T cell therapy protocols. In a particular embodiment, said immunotherapy does not involve the use of an anti-Lag3 antibodies or inhibitors. In another particular embodiment, said immunotherapy is a Lag-3 inhibitor. In a particular embodiment, the subject is further treated with (or the method further comprises administration of) an adoptive cell therapy composition as disclosed herein (e.g. prepared by administering to, or expressing in, a T cell population, an oligonucleotide of the invention, in an amount and under conditions suitable for inducing or enhancing splice switching in the T cell population).

In some embodiments, the oligonucleotides to be used in the compositions and methods of the invention are 15-30 nucleotides in length, specifically hybridizable with a nucleic acid target selected from the group consisting of SEQ ID NOs: 4, 6 or 7, and not with a target as set forth in SEQ ID NO: 8. In some embodiments said oligonucleotides are at least 90%, at least 95% or at least 98% complementary to the nucleic acid target. In a particular embodiment, said oligonucleotides are 18-22 nucleotides in length. In another embodiment said oligonucleotides are specifically hybridizable with SEQ ID NO: 6 or 7. In another embodiment said oligonucleotides have the nucleic acid sequence as set forth in any one of SEQ ID NOs: 1-2. In another embodiment said oligonucleotides are single-stranded RNA molecules. In another embodiment said oligonucleotides are derivatized by one or more backbone and/or sugar chemical modifications. In another embodiment said oligonucleotides comprise one or more 2' sugar modifications. In another embodiment said modifications are selected from the group consisting of 2'-O-Methyl (2'-O-Me), 2'-O-methoxyethyl (2'-MOE), and combinations thereof. In another embodiment said oligonucleotides are selected from the group consisting of SEQ ID NOs: 1 and 2 and/or are fully derivatized by 2'-O-Me or 2'-MOE. In another embodiment said oligonucleotides are splice-switching oligonucleotides.

Adoptive Cell Therapy

In another aspect, there is provided a T cell composition prepared as described herein, suitable for adoptive transfer into a recipient subject in need thereof. As used herein, and unless otherwise specified, the term "adoptive transfer" refers to a form of passive immunotherapy where previously sensitized immunologic agents (e.g., cells or serum) are transferred to the recipients. The phrases "adoptive transfer immunotherapy", "adoptive cell therapy" and "adoptive cell immunotherapy" are used interchangeably herein to denote a therapeutic or prophylactic regimen or modality, in which effector immunocompetent cells, such as the T cell compositions of the invention, are administered (adoptively transferred) to a subject in need thereof, to alleviate or ameliorate the development or symptoms of cancer or infectious diseases.

T lymphocytes (T cells) are one of a variety of distinct cell types involved in an immune response. The activity of T cells is regulated by antigen, presented to a T cell in the context of a major histocompatibility complex (MHC) molecule. The T cell receptor (TCR) then binds to the MHC-antigen complex. Once antigen is complexed to MHC, the MHC-antigen complex is bound by a specific TCR on a T cell, thereby altering the activity of that T cell. Proper activation of T lymphocytes by antigen-presenting cells requires stimulation not only of the TCR, but the combined and coordinated engagement of its co-receptors.

T helper cells (TH cells) assist other white blood cells in immunologic processes, including maturation of B cells into plasma cells and memory B cells, and activation of cytotoxic T cells and macrophages. These cells are also known as CD4$^+$ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response.

Cytotoxic T cells (Tc cells, or CTLs) destroy virus-infected cells and tumor cells, and are also implicated in transplant rejection. These cells are also known as CD8$^+$ T cells since they express the CD8 glycoprotein at their surfaces. These cells recognize their targets by binding to antigen associated with MHC class I molecules, which are present on the surface of all nucleated cells.

Regulatory T cells (T$_{reg}$ cells), formerly known as suppressor T cells, are crucial for the maintenance of immunological tolerance. Their major role is to shut down T cell-mediated immunity toward the end of an immune reaction and to suppress autoreactive T cells that escaped the process of negative selection in the thymus.

The TCR is a complex of integral membrane proteins, wherein stimulation by specific MHC-presented antigen recognition and binding by the clonotype-specific α/β heterodimer leads to activation of transcription and subsequent proliferation and effector functions (such as cytotoxic activity in CD8$^+$ T cells and cytokine secretion in CD4$^+$ T cells). This activation involves other subunits of the receptor complex as detailed below that couple the extracellular liganding event to downstream signaling pathways such as protein phosphorylation, the release of inositol phosphates and the elevation of intracellular calcium levels.

The intracellular portions of the CD3 γ, δ, ε, and ζ subunits contain copies of a sequence motif termed ITAMs (immunoreceptor tyrosine-based activation motifs). ITAMs can serve as protein tyrosine kinase substrates and, after phosphorylation, as binding sites for SH2 domains of yet other kinases. The regulation and mechanism of the recruitment of protein kinases to the activated T cell receptor involves members of both the Syk family (ZAP-70) and Src family (Lck) of kinases.

TCR stimulation as detailed above may be antigen-specific or antigen non-specific (Polyclonal). Suitable antigen-specific TCR activators include antigens bound to MHC molecules, typically in the context of antigen presenting cells (APC). Polyclonal TCR activators are capable of initiating the signal transduction and transcriptional activation pathways associated with specific TCR engagement in the absence of specific antigens. Suitable polyclonal T cell activators include antibodies that bind and crosslink the T cell receptor/CD3 complex, e.g. subunits as described herein. Exemplary antibodies that crosslink the T cell receptor include the HIT3a, UCHT1 and OKT3 monoclonal antibodies. The stimulation is provided at an amount and under conditions as known in the art so as to induce the above-mentioned functional effects.

Typically, compositions for adoptive cell transfer are prepared by methods including activating a T cell population by a TCR stimulation, and expansion of the cells to obtain a therapeutically effective amount of effector T cells for administration. Such methods include but are not limited to, Rapid Expansion Protocols (REP).

In various embodiments, the TCR stimulation may be antigen non-specific (performed, for example, using antibodies specific to CD3 that activate the receptor upon binding, e.g. OKT3) or antigen-specific (using suitable antigen presenting cells and antigen). In the context of cancer treatment, antigen-specific stimulation typically employs stimulation to tumor-associated antigens. The term "tumor-associated antigen" (TAA) refers to any protein, peptide or antigen associated with (carried by, expressed by, produced by, secreted by, etc.) a tumor or tumor cell(s). Tumor-associated antigens may be (nearly) exclusively associated with a tumor or tumor cell(s) and not with healthy normal cells or may be over expressed (e.g., 2 times, 5 times, 10 times, 50 times, 100 times, 1000 times or more) in a tumor tissue or tumor cell(s) compared to healthy normal tissue or cells. More particularly, a TAA is an antigen capable of being presented (in processed form) by MHC determinants of the tumor cell. Hence, tumor-associated antigens are likely to be associated only with tumors or tumor cells expressing MHC molecules. Non-limitative examples of well-known TAA are MART-1, gp100 $_{209\text{-}217}$, gp100 $_{154\text{-}163}$, CSPG4, NY-ESO, MAGE-A1, Tyrosinase.

In some embodiments, one commonly used approach for stimulating proliferation, in particular of CD8$^+$ T cells, is the incubation of T cells with soluble anti-CD3 antibody in the presence of Fc receptor-bearing accessory cells (feeder cells), an approach designated the REP. Antibody "presented" to T cells in this manner generates a more effective proliferative signal than soluble anti-CD3 alone or anti-CD3 immobilized on a plastic surface. In the treatment of cancer, adoptive cell therapy typically involves collecting T cells that are found within the tumor of the patient (referred to as tumor-infiltrating lymphocytes, TIL), which are encouraged to multiply ex vivo using high concentrations of IL-2, anti-CD3 and allo-reactive feeder cells. These T cells are then transferred back into the patient along with exogenous administration of IL-2 to further boost their anti-cancer activity.

Thus, according to certain additionally advantageous embodiments, activation and/or expansion (e.g. as part of a REP protocol) is performed in the presence of feeder cells. The term "feeder cells" generally refers to cells of one type that are co-cultured with cells of a second type, to provide an environment in which the cells of the second type can be maintained and proliferated. For the purpose of the present invention, this term specifically refers to Fc receptor-bearing accessory cells, which are typically allo-reactive with the T cell containing population to be propagated. In other words, the feeder cells need not be histocompatible with the T-cell containing population to be propagated, and in certain advantageous embodiments the two populations typically HLA-mismatched. A typical example of feeder cells used in embodiments of the invention is allogeneic normal donor peripheral blood mononuclear cells, PBMC. Typically and advantageously, the use of such feeder cells is performed in conjunction with antigen non-specific TCR stimulation, e.g. by incubation with antigen non-specific stimulating antibodies, as detailed herein.

In another embodiment, adoptive transfer T cell compositions are prepared with irradiated PBMC (incapable of proliferation) as feeder cells. For example, PBMC may conveniently be attenuated by irradiation by exposing the cells to 6000RAD. In another embodiment, adoptive transfer T cell compositions are prepared with artificial antigen presenting entities including antigen presenting cells and inert particles carrying antigens, to provide antigen-specific stimulation.

In various embodiments, T cell expansion may be performed for at least 5 and typically at least 6, 7, or 8 days. Typically, expansion is performed for up to about 16, 15, 14, 13, or 12 days, for example 5-15 days, e.g. 6-12 or more typically 8-15 days. In another embodiment, the population comprises CD8$^+$ T cells. In another embodiment, the T cells are CD8$^+$ T cells. In another embodiment, the cells are further genetically engineered or modified (e.g. to exert a desired antigen specificity). For example, in another embodiment, the cells are lymphocytes (e.g. purified T cells such as CTL) genetically engineered to express a TCR pre-designed to re-direct them against cancer cells or against pathogens (e.g. viruses). By means of a non-limitative example, T cells engineered to express a TCR directed against NY-ESO-1, an antigen expressed on many solid tumors, e.g. synovial sarcoma. In another embodiment, the cells are peripheral blood mononuclear cells genetically engineered to express a chimeric antigen receptor (CAR) to re-direct them against cancer cells or pathogens. For example, without limitation, CAR-T cells targeting CD19 may be used for the treatment of B cell malignancies such as acute lymphoblastic leukemia. In another embodiment, the cells are peripheral blood mononuclear cells genetically engineered to express genes that enhance their biological function. For example, without limitation, such genes may include membrane bound cytokine and cytokine receptor (e.g. IL-2 and IL-2R). In another embodiment the population comprises CD4$^+$ T cells. In another embodiment the population comprises a combination of CD8$^+$ T cells and CD4$^+$ T cells.

The cell composition may comprise a T cell-containing population in an effective amount. For example, an amount effective for adoptive transfer immunotherapy is an amount sufficient to induce or enhance a beneficial immune response such as an anti-tumor response, e.g. $10^6$ to $10^{12}$ cells. It is to be understood, that while cell preparations suitable for in vivo administration, particularly for human subjects, may contain pharmaceutically acceptable excipients or diluents, such preparations are sufficiently devoid of contamination by pathogens, toxins, pyrogens and any other biological and non-biological agents which are not recognized to be pharmaceutically acceptable. For example, without limitation, T cells for adoptive transfer immunotherapy may conveniently be suspended in an injection suitable buffer that contains sterile saline with 2% human albumin, and optionally IL-2 (e.g. 3001 U/ml).

According to certain preferable embodiments, the cell composition is histocompatible with the subject to be treated (e.g. autologous cells or MHC II-matched allogeneic cells).

The term "histocompatibility" refers to the similarity of tissue between different individuals. The level of histocompatibility describes how well matched the patient and donor are. The major histocompatibility determinants are the human leukocyte antigens (HLA). HLA typing is performed between the potential donor and the potential recipient to determine how close an HLA match the two are. The term "histocompatible" as used herein refers to embodiments in which all six of the HLA antigens (2 A antigens, 2 B antigens and 2 DR antigens) are the same between the donor and the recipient.

However, in other embodiments, donors and recipients who are "mismatched" at two or more antigens, for example 5 of 6, or in other embodiments, 4 of 6 or 3 of 6 match, may be encompassed by certain embodiments of the invention, despite the donor and recipient not having a complete match. The term "substantially histocompatible" as used herein refers to embodiments in which five out of six of the HLA antigens are the same between the donor and the recipient.

In some embodiments of the methods of the invention, expanding the T cell population so as to obtain a T cell composition adapted for adoptive transfer immunotherapy comprising an effective amount of the resulting T cell population, is performed by a REP protocol comprising providing the T cell population with a TCR stimulation and at least one co-stimulation. In a particular embodiment, the expansion is performed by providing said cell population with a TCR stimulation and a SLAMF6-mediated stimulation (e.g. using an isolated SLAMF6 ectodomain, SLAMF6-specific agonistic antibody, or SLAMF6 homotypic engagement).

Thus, in some embodiments, provided are methods for preparing a T cell composition adapted for adoptive transfer immunotherapy, comprising the step of administering to, or expressing in, a T cell population, an oligonucleotide as defined herein, in an amount and under conditions suitable for inducing or enhancing splice switching (in particular in the SLAMF6 gene) in the T cell population. In various embodiments, the oligonucleotide is a SLAMF6 expression-modulating oligonucleotide of 15-30 nucleotides in length, specifically hybridizable with a nucleic acid target selected from the group consisting of SEQ ID NOs: 4, 6 or 7, and not with a target as set forth in SEQ ID NO: 8. In some embodiments said oligonucleotides are at least 90%, at least 95% or at least 98% complementary to the nucleic acid target. In a particular embodiment, said oligonucleotides are 18-22 nucleotides in length. In another embodiment said oligonucleotides are specifically hybridizable with SEQ ID NO: 6 or 7. In another embodiment said oligonucleotides have the nucleic acid sequence as set forth in any one of SEQ ID NOs: 1-2. In another embodiment said oligonucleotides are single-stranded RNA molecules. In another embodiment said oligonucleotides are derivatized by one or more backbone and/or sugar chemical modifications. In another embodiment said oligonucleotides comprise one or more 2' sugar modifications. In another embodiment said modifications are selected from the group consisting of 2'-O-Methyl (2'-O-Me), 2'-O-methoxyethyl (2'-MOE), and combinations thereof. In another embodiment said oligonucleotides are selected from the group consisting of SEQ ID NOs: 1 and 2 and/or are fully derivatized by 2'-O-Me or 2'-MOE. In another embodiment said oligonucleotides are splice-switching oligonucleotides.

In another embodiment, the method comprises:
a. providing a T cell population comprising CD8$^+$ T cells,
b. administering to, or expressing in the T cell population, one or more SLAMF6 expression-modulating oligonucleotides of the invention, in an amount and under conditions suitable for inducing or enhancing splice switching in said T cell population, and
c. expanding said T cell population,
so as to obtain a T cell composition adapted for adoptive transfer immunotherapy comprising an effective amount of the resulting T cell population.

According to various other specific embodiments, the composition is prepared according to specific protocols and parameters as disclosed herein, for example by the REP protocols described above. In another embodiment, step b may be performed by methods known in the art, for example the oligonucleotides may be administered to the cells e.g. by electroporation, using Nucleofector technology, (AMAXA), or by other transfection methods e.g. liposome-mediated transfer. The oligonucleotides may also be expressed in the cells following transfection or infection with a suitable construct (including, but not limited to viral vectors, e.g. AAV-based vectors) encoding the oligonucleotides. Exemplary conditions for inducing or enhancing splice switching are provided throughout the specification and Examples herein.

For instance, in some embodiments, expression-modulating oligonucleotides of the invention may be used at step b. at a concentration of about 2.5-20 μM, e.g. 5-10, or 5-7.5 μM, to be transfected by electroporation. e.g. by an exponential decay electroporation system or by a system enabling intranuclear transfection such as nucleofection.

For example, without limitation, splice-switching may be induced in T cell lines such as Jurkat cells by transfection of 2.5-20 μM, typically 5-10 μM (e.g., 5 μM for 5-10×10$^6$ cells in 330 μl RPMI medium), for instance using an exponential decay electroporation system such as ECM 630 Electro Cell manipulator (BTX Harvard apparatus) Exponential electroporation—250V, 300 μF, 1000Ω (e.g. in Biorad 0.2 cm cuvettes). In PBMCs, the ASOs may be used at 2.5-15 μM, typically 5-7.5 μM (e.g. 5 μM for 5-10×10$^6$ cells in 100 μl nucleofector solution). Electroporation may be performed for instance using a nucleofection system e.g. AMAXA (Lonza), nucleofector program T-023. In TILs, the ASOs may be used at 2.5-15 μM, typically 5-7.5 μM (e.g. 5 μM for 2.5×10$^6$ cells to 2.5×10$^7$ cells in 1 ml of OptiMem medium). Electroporation may be performed e.g. using an exponential decay electroporation system such as ECM 630 Electro Cell manipulator (BTX Harvard apparatus) Exponential electroporation 260V, 1050 μF, infinite resistance in Biorad 0.2 cm cuvettes.

In various embodiments, step b. is performed so as to induce or enhance splice-switching in the SLAMF6 gene, e.g. measurable as enhancement in the ratio of the SLAMF6$^{var3}$ to SLAMF6$^{var1}$ splice transcripts by 1.5-3.5-fold, e.g. by about twofold.

In another embodiment, step c is performed by REP. In another embodiment, step c is performed by providing said cell population with a TCR stimulation and at least one co-stimulation. In another embodiment, step c is performed by providing said cell population with a TCR stimulation and a SLAMF6-mediated stimulation.

In some exemplary embodiments, step c. comprises incubating said cell population with IL-2 and an anti-CD3 antibody in the presence of irradiated PBMC feeder cells. For example, without limitation, expansion of TIL may conveniently be performed at IL-2 concentrations of between 3000 to 6000 U/ml, and the anti-CD3 antibody may be used at a concentration of e.g. about 30 μg/ml. exemplary ratios of feeder cells to T cells may be of between 1:50 and 1:200. In other non-limitative examples, expansion of engineered T cells may conveniently be performed at IL-2 concentration of between 100 U/ml to 3000 U/ml, and anti-CD3 antibody may be used at a concentration of between 30 to 60 μg/ml.

In other exemplary embodiments, step c. may conveniently employ the use of immobilized antibodies (e.g. anti-CD3 and anti-CD28 antibodies), in the absence of feeder cells. Suitable expansion systems involving bead-conjugated antibodies or nanoparticles are known in the art and are commercially available e.g. from Gibco, Waltham, MA (DynaBeads®) or Miltenyi (TransAct™). In some embodiments, the TCR stimulation is a CD3-directed stimulation and the co-stimulation is a CD28-directed stimulation.

In some embodiments, bead-immobilized-anti-CD3 and anti-CD28 antibodies are used. In other embodiments, beadimmobilized-anti-CD3, anti-CD28 and anti-CD137 antibodies are used. For example, without limitation, cells may be seeded in a bead:PBMC ratios of 3:1 (low cell seeding) to 2:1 (high cell seeding) and then mixed at room temperature for 10 minutes using a rotating cell mixer at a concentration of $4\times10^6$ to $6\times10^6$ cells/mL. Cells may be seeded at $30\times10^6$ cells (e.g. PBMCs) per Quantum system (low seeding) to $85\times10^6$ cells per Quantum system (high seeding). Cell-bead mixtures may be diluted to 50 mL medium without IL-2 and added to a cell inlet bag (Terumo BCT), then loaded into the IC loop of the Quantum system (e.g. when used with DynaBeads®, Gibco, Waltham, MA).

In another non-limitative example, a polymeric nanomatrix conjugated to CD3 and CD28 antibodies (e.g. Trans-Act™ by Miltenyi) is utilized. For example, without limitation, purified T cells may be activated at a surface density of about $1\times10^6$ cells per cm$^2$ and PBMCs with up to about $2\times10^6$ per cm$^2$. Stimulation may be performed in a 48-well plate of up to about $1\times10^6$ purified T cells or up to about $2\times10^6$ PBMCs in a total volume of 990 μL of e.g. Tex-MACS™ Medium supplemented with about 20 IU/mL Human IL-2 or about 155 U/mL Human IL-7 and about 290 U/mL Human IL-15.

In one embodiment, step c is performed prior to step b (for example, when the method includes administering the one or more SLAMF6 expression-modulating oligonucleotides to the cells). In another embodiment, step b is performed prior to step c (for example, when the method includes expressing in the T cell population the one or more SLAMF6 expression-modulating oligonucleotides). In another embodiment, steps b and c are performed concomitantly. According to exemplary embodiments, a T cell composition adapted for adoptive transfer immunotherapy prepared by a method as disclosed herein, and in particular a method comprise administering the one or more SLAMF6 expression-modulating oligonucleotides to the cells (e.g. by transfection), are amenable for administering to a subject in need thereof within 12 hours of administration of said oligonucleotide to said cells, and up to about 5 to 7 days thereafter. Accordingly, in some embodiments, the methods of the invention further contain the step of administering the resulting T cell composition adapted for adoptive transfer immunotherapy to a subject in need thereof within 12 hours and up to about 5-7 days of step b.

In another embodiment, said cell population (e.g. as provided in step a) is selected from the group consisting of TIL, tumor-specific T cell clones, and genetically modified T cells (e.g. expressing an exogenous tumor-specific TCR). In another embodiment said cell population expresses a CAR.

In some embodiments, a T cell composition adapted for adoptive transfer immunotherapy prepared by a method of the invention is characterized by enhanced functional capacity, e.g. by enhanced anti-cancer functions as disclosed herein. For example, the T cell composition may be characterized by an enhancement of about 2-6 folds in IFN-γ secretion compared to an equivalent T cell composition prepared using a conventional method such as standard (non-improved) REP. in various embodiments, said T cell composition is characterized by an enhancement of at least 1.5-fold and typically 2-6 folds in IFN-γ secretion, Tbet expression and/or Runx3 expression compared to the equivalent control composition. In another embodiment, the enhanced anti-tumor activity is measured by in vitro and/or in vivo parameters as disclosed herein. Further, the T cell composition is characterized by modulation of expression in SLAMF6 splice transcripts as disclosed herein. In some embodiments, said enhancements and characteristics are evident from about 12 hours and up to about 5-7 days of step b.

In another embodiment, there is provided a T cell composition adapted for adoptive transfer immunotherapy prepared by the method. In various embodiments, the T cell composition is as disclosed and exemplified herein. In other embodiments, said T cell compositions may be used in the methods of the invention, e.g. treating cancer and/or for inducing or enhancing anti-tumor immunity, as described herein. In a particular embodiment the tumor is a solid tumor (e.g. melanoma, renal cell carcinoma, lung cancer, breast cancer, or head and neck cancer). Each possibility represents a separate embodiment of the invention.

As used throughout the specification herein, and unless indicated otherwise, the term "about" refers to ±10%.

The following examples are presented in order to more fully illustrate some embodiments of the invention. They should, in no way be construed, however, as limiting the broad scope of the invention.

EXAMPLES

Example 1. ASOs Directed to Previously Suggested Regulatory Regions 20-mer ASOs, designed to target various regions at the intron-exon junctions either upstream or downstream to exon 2 (Hajaj et al., 2018), were synthesized using 2-O-Me modified nucleosides. The ASOs were transfected to Jurkat T cells ($5\times10^6$ cells in 330 μl RPMI medium, 5 μM of the ASO) by electroporation in Biorad 0.2 cm cuvettes using ECM 630 Electro Cell manipulator (BTX Harvard apparatus) Exponential electroporation—250V, 300 μF, 1000Ω. 24 hours later, RNA was extracted using GenElute Mammalian Total RNA kit (Sigma, RTN70) according to the manufacturer's protocol. SLAMF6 isoforms were detected by RT-PCR using primers directed to exons 1 and 3, as follows: GCGGAAAGCATGTTGTGGCTG (SEQ ID NO: 11) and GGAGACAGTGAGGTTTGGCTG (SEQ ID NO: 12), respectively.

A representative ASO, herein designated ASO4, has the nucleic acid sequence UUGUGAAACUACAUUCCCUG (SEQ ID NO: 9) and specifically hybridizes with a target sequence at the intron 1—exon 2 junction, as follows: CAGGGAATGTAGTTTCACAA (SEQ ID NO: 10). The positions of the ASOs are schematically represented at FIG. 1C, top, and the results of the isoform expression following treatment with ASO4 are presented in FIG. 1A. A scrambled ASO that does not specifically bind to the SLAMF6 transcript, having the nucleic acid sequence TGACCGAAAA-GUCATCUCAA (SEQ ID NO: 5), was used as a control.

Figure 1C:
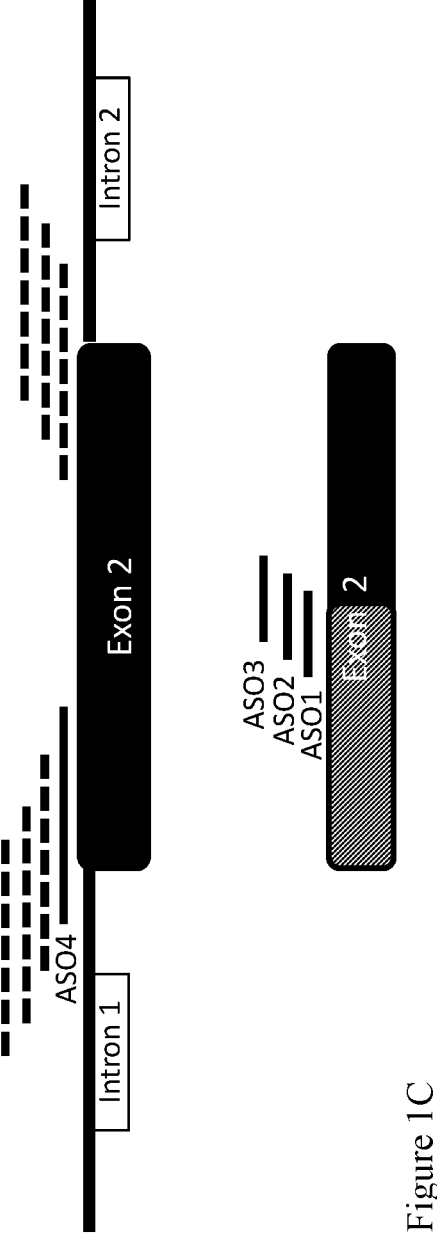
FIG. 1C provides a scheme illustrating the position of the tested ASOs with respect to SLAMF6 exon 2.

As can be seen in FIG. 1A, no modulation of SLAMF6 isoform expression was observed upon treatment with ASO4. None of the other ASOs directed to the regions spanning the known exon 2—intron junctions (dashed lines in FIG. 1C, top) was identified as a functional SSO either. An additional, partially overlapping ASO, directed to a target sequence at the intron 1—exon 2 junction, hitherto identified as exhibiting modulation of SLAMF6 isoform expression (Hajaj et al., 2018), failed to demonstrate any augmentation of T cell functions when tested as described in Example 3. Thus, none of the ASOs designed to bind target regions at the vicinity of predicted exon 2 splice sites and other cis-acting elements, were capable of altering the abundance of SLAMF6 isoforms in a consistent manner associated with any efficacy in modulating T cell activity.

Example 2. Identification of a New Target Region for Modulating SLAMF6 Splicing Additional ASOs, with sequences designed to bind various target sequences within exon 2, were also examined in similar experiments. The positions of these partially overlapping ASOs are schematically represented at FIG. 1C, bottom (in which the right side, presented in black, represents the portion of exon 2 present in both variants, and the left, light-shaded side, represents the portion of exon 2 present only in SLAMF6$^{var1}$. The sequences of the ASOs, designated ASO1, ASO2 and ASO3, are GGGUAC-UAUGAAGGCAAGAG, UCAUGGGGUAC-UAUGAAGGC and UGGUUUCAUGGGGUACUAUG (SEQ ID NOs: 1-3, respectively). The target sequences specifically hybridizable with these ASOs are as set forth in SEQ ID NOs: 6-8, respectively (CTCTTGCCTTCAT-AGTACCC, GCCTTCATAGTACCCCATGA and CAT-AGTACCCCATGAAACCA). The ASOs were also synthesized using 2-O-Me modified nucleosides and used in the same concentrations as described in Example 1. The results are presented in FIG. 1B.

As can be seen in FIG. 1B, all tested ASOs (ASO1-3) exhibited modulation of SLAMF6 isoform expression, compared to the expression observed upon treatment with the control ASO ("scrambled"). Specifically, the levels of the SLAMF6$^{var1}$ transcript were reduced and the levels of the SLAMF6$^{var4}$ transcript were enhanced upon treatment with ASO1, ASO2 and ASO3. However, the ASOs differed in their effect on the SLAMF6$^{var3}$ transcript, the levels of which were enhanced or retained when the cells were treated with ASO1 or ASO2, while ASO3 appeared to show a reduction in the SLAMF6$^{var3}$ transcript level.

Example 3. Changes in the Expression Ratio of SLAMF6 Splice Products Following Treatment with Splice-Switching ASOs is Correlated with an Improved Functional Capacity For evaluating the effects of the ASOs on T cell function, four increasing concentrations (0.5, 1, 2.5 and 5 μM) of each of ASO1, ASO2, ASO3 or the control ASO (scrambled, scr; 5 μM) were transfected to Jurkat cells (5×10$^6$ cells in 330 μl RPMI medium) by electroporation as described in Example 1. 24 hours later, the cells were collected and activated with a combination of PMA (200 ng/ml) and Ionomycin (300 ng/ml) for 48 hours. Next, the conditioned media were collected and IL-2 secretion was evaluated using ELISA (DY202 Kit, Human IL-2 DuoSet ELISA (R&D)). The results are presented in FIG. 2A (effect on SLAMF6 isoform transcript levels) and FIG. 2B (IL-2 secretion).

Figure 2A:
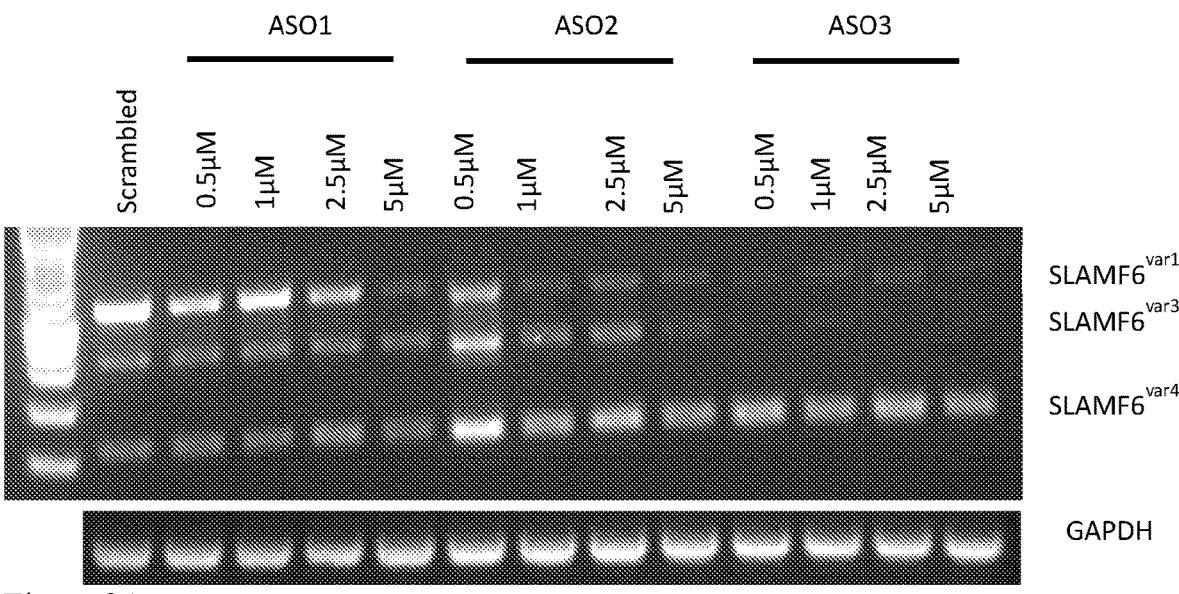
FIG. 2A presents the expression patterns of SLAMF6 isoforms in Jurkat cells following treatment with different concentrations of the tested ASOs.
Figure 2B:
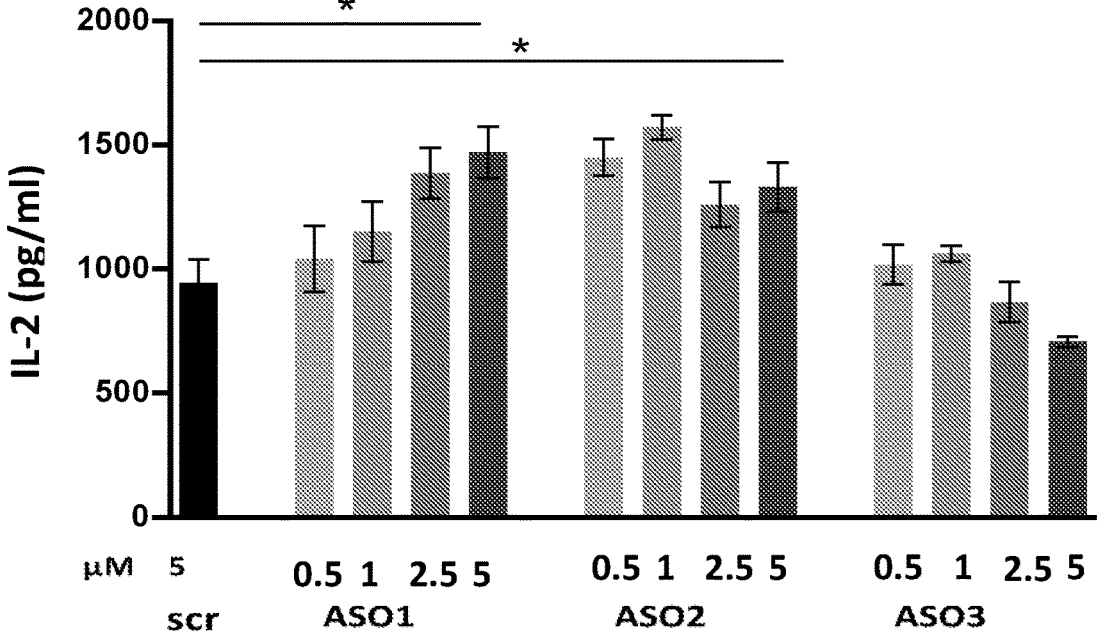
FIG. 2B shows IL-2 secretion determined using ELISA following PMA and ionomycin activation of the cells manipulated by the ASOs. Student T test * $p < 0.05$.

As can be seen in FIGS. 2A-2B, two out of the three ASOs, namely ASO1 and ASO2, significantly enhanced IL-2 secretion induced by activation stimuli. However, ASO3 did not induce similar effects (FIG. 2A).

Thus, a novel sequence within exon 2 was identified as a target for inducing splice-switching and modulating the abundance of SLAMF6 isoforms. Specifically, ASOs directed to SEQ ID NOs: 6 and 7, but not to SEQ ID NO: 8, were capable of improving T cell reactivity to activation stimuli. Based on the findings described in FIGS. 2A-2B, the novel target sequence was identified as residing within SEQ ID NO: 4, as follows:

```
ATCTCTTGCCTTCATAGTACCCCATGAAA.
```

Example 4. SLAMF6 Isoform Modulation in PBMC and TIL, and Improved Functional Capacity Next, the ability of the ASOs to modulate SLAMF6 isoform expression in other T cell types was determined. To this end, peripheral blood leukocytes (PBMC) were purified from healthy human donors' buffy coats (Hadassah Blood Bank); human tumor-infiltrating lymphocytes (TIL 209 clone) were obtained as follows. Microcultures were initiated and expanded from tumor specimens taken from resected metastases of melanoma patients, according to standard procedure. Human lymphocytes were cultured in complete medium (CM) consisting of RPMI 1640 supplemented with 10% heat-inactivated human AB serum, 2 mmol/l L-glutamine, 1 mmol/l sodium pyruvate, 1% non-essential amino acids, 25 mmol/l HEPES (pH 7.4) 50 μmol/l 2-ME, and combined antibiotics (all from Invitrogen Life Technologies). CM was supplemented with 6000 IU/ml recombinant human IL-2 (rhIL-2, Chiron).

ASO1, ASO2 or the control ASO, were transfected into the cells using AMAXA (Lonza), nucleofector program T-023 (5×10$^6$ cells, 5 μM ASO, in 100 μl nucleofector solution). Following transfection, RNA was extracted and splicing of SLAMF6 was detected by RT-PCR using primers from exons 1 and 3, as described in Example 1. The results are shown in FIG. 3.

Figure 3:
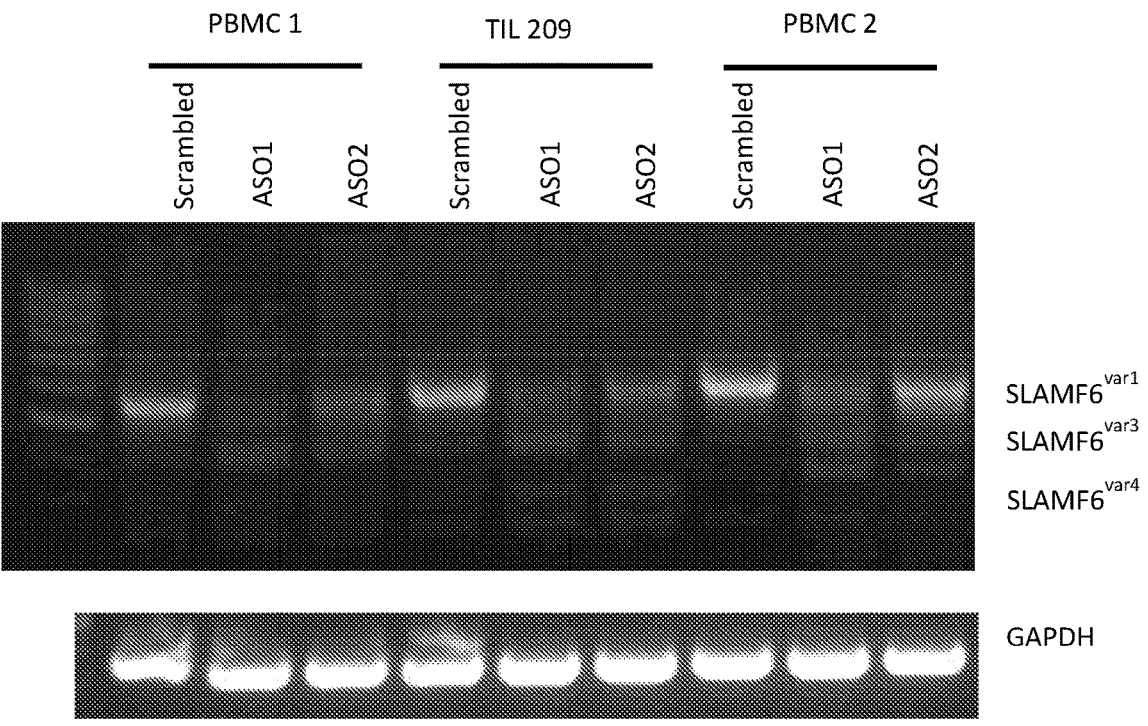
FIG. 3 presents the expression patterns of SLAMF6 isoforms in PBMC and TIL following treatment with different concentrations of the tested ASOs.

As can be seen in FIG. 3, both ASO1 and ASO2 were capable of enhancing the ratio of the SLAMF6$^{var3}$ transcript to SLAMF6$^{var1}$ transcript in both PBMC and TIL.

In a separate experiment, PBMC from two healthy donors were electroporated with ASO1 or a control ASO (as in previous experiments), essentially as described above. 24 hours post electroporation, the cells were activated with plate-bound anti CD3 antibody (1 μg/ml, overnight incubation). At the end of the activation, IFNγ secretion was measured using ELISA. The results are presented in FIG. 5.

Figure 5:
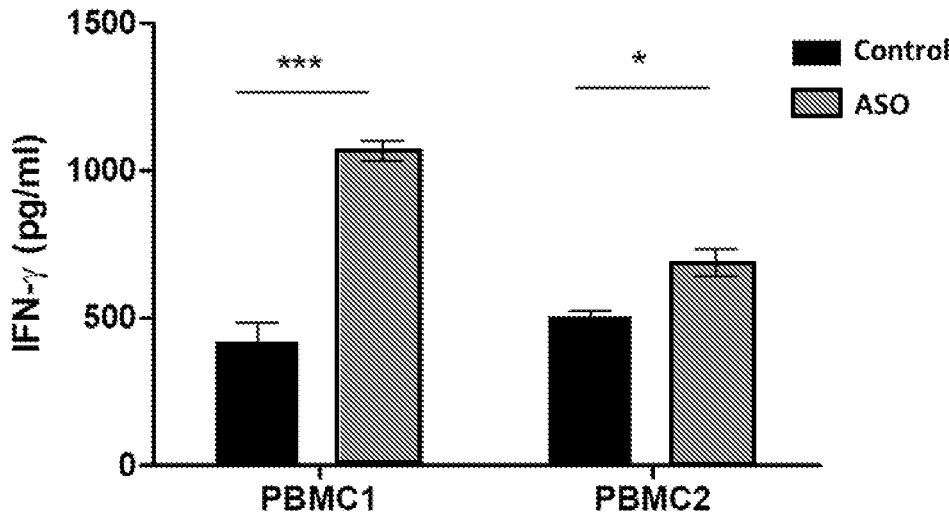
FIG. 5 demonstrates that electroporation of splice-switching ASO to PBMC leads to enhanced activation-induced IFNγ. Student T test * $p < 0.05$, * $p < 0.001$

As can be seen in FIG. 5, incubation with ASO1 ("ASO") led to higher IFNγ secretion post activation than incubation with the control ASO ("Control"). The enhanced activation was statistically significant in both PBMC samples (from donors 1 and 2, "PBMC1", and "PBMC2", respectively).

Example 5. Long-Term Effects of 2'-O-Methoxyethyl-Modified ASOs

2'-O-methoxyethyl (MOE)-modified ASOs corresponding to the nucleic acid sequences of ASO1, ASO2 and the control ASO were synthesized using 2'-MOE-derivatized nucleosides. The ASOs were transfected to Jurkat cells as described in Example 1. Next, RNA was extracted at different time points following transfection, namely after 24 hr, 48 hr, 96 hr and one week of transfection, and SLAMF6 isoform transcripts were detected by RT-PCR as described in Example 1. The results are presented in FIG. 4.

Figure 4:
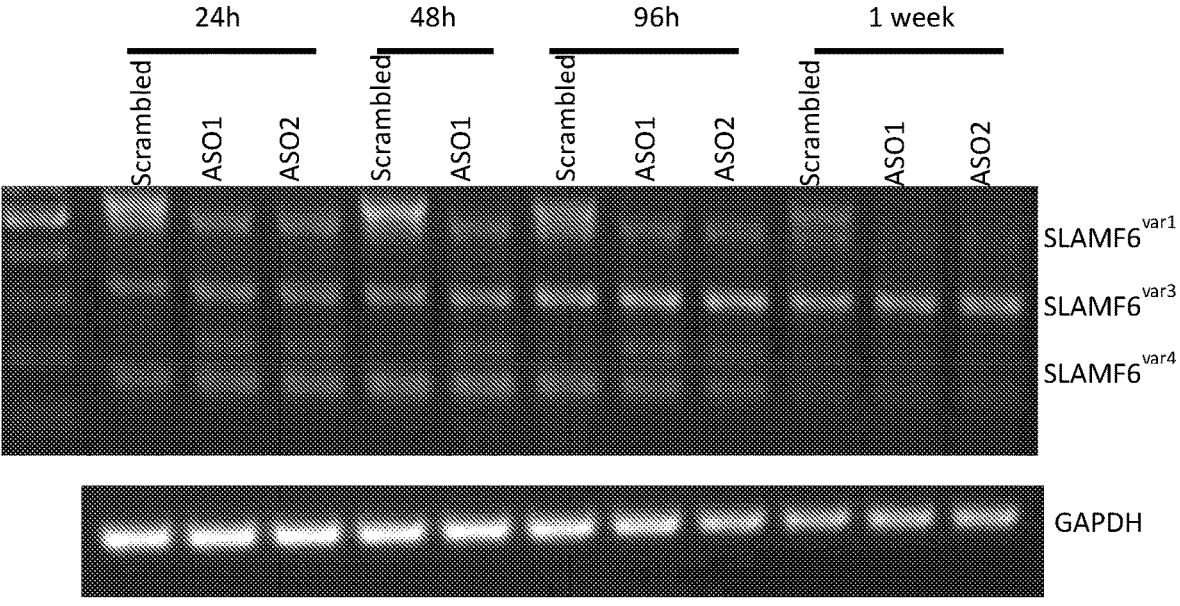
FIG. 4 presents the expression patterns of SLAMF6 isoforms in Jurkat cells at different time points following treatment with 2'-O-methoxyethyl-modified ASOs.

As can be seen in FIG. 4, both ASO1 and ASO2 were capable of enhancing the ratio of the SLAMF6$^{var3}$ transcript to SLAMF6$^{var1}$ transcript. The effect was long-lasting and was apparent for at least a week, and surprisingly seemed to become more pronounced over time. The results demonstrate the applicability of the tested ASOs for clinical applications, requiring persistent pharmacological effects.

Example 6. SLAMF6 Isoform Modulation in TIL Treated with Modified ASOs

Human TIL (209 clone) were electroporated with either negative control ASO ("scr"), or with ASOs corresponding to the nucleic acid sequences of ASO1, modified by either 2-O-Methyl (2'-OME) derivatized nucleosides ("ASO company1") or 2'-MOE ("ASO company 2"). 24 h post electroporation, RNA was extracted from the cells, and the expression of SLAMF6 isoforms was tested. The experiment was performed essentially as described in Example 4. The results are presented in FIG. 6.

Figure 6:
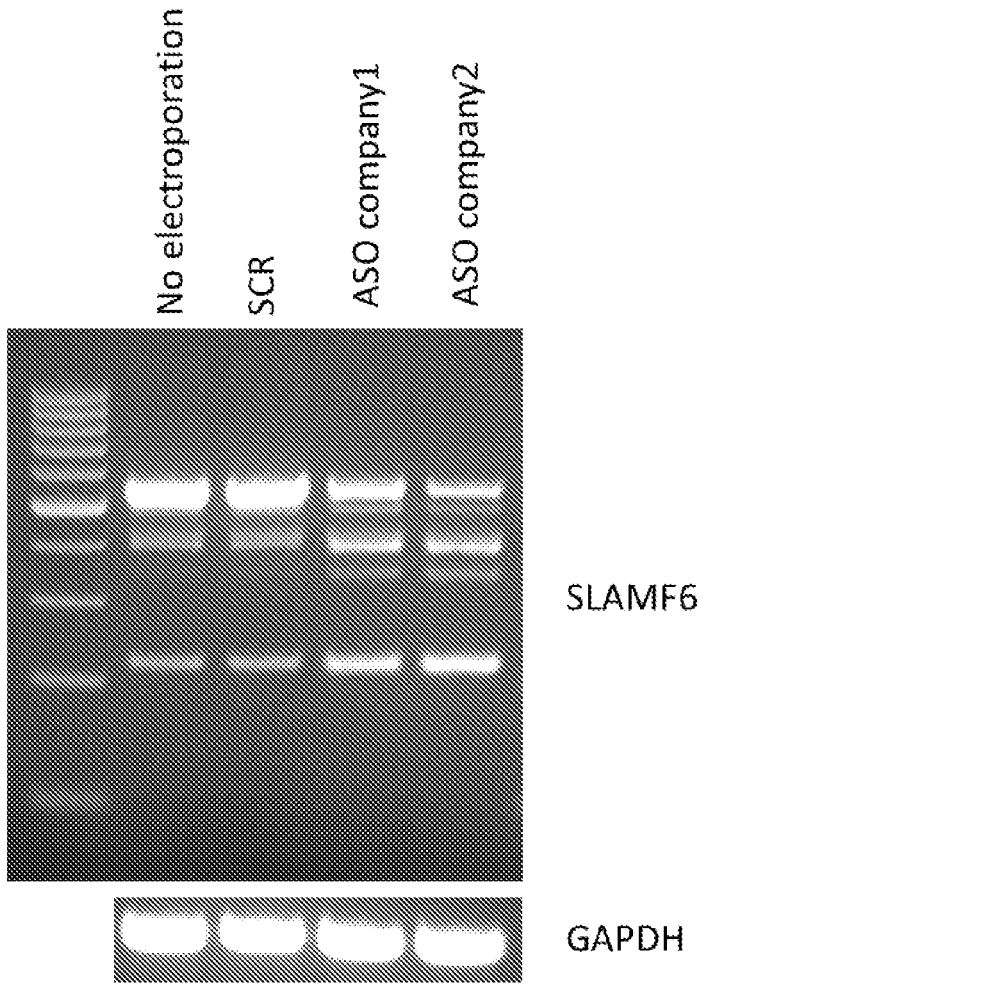
FIG. 6** presents the expression patterns of SLAMF6 isoforms in TIL following treatment with ASOs modified with 2-OME ("ASO company1") or 2-MOE ("ASO company 2"), a negative control ASO ("scr"), or untreated cells ("No electroporation").

As can be seen in FIG. 6, ASO1 modified by either 2'-OME or 2'-MOE induced modulation of expression of SLAMF6 isoforms, enhancing the ratio of the SLAMF6$^{var3}$ transcript to SLAMF6$^{var1}$ transcript compared to the control cells.

Example 7. Anti-Tumor Activity In Vivo

Figure 7A:
FIG. 7A is a scheme illustrating the experimental layout of the in vivo model.
Figure 7A:
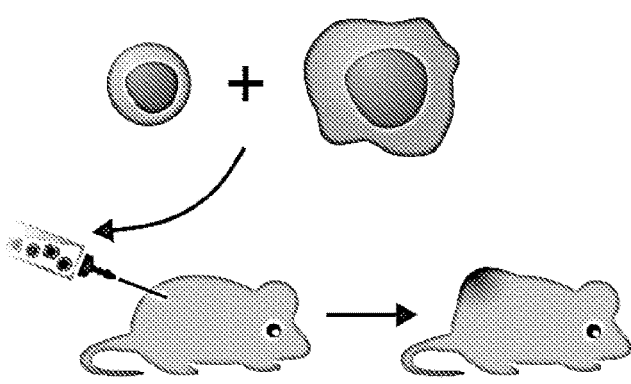

The effect of the tested splice-switching ASO on in vivo anti-tumor cytotoxicity was examined by Winn assay, according to the experimental scheme illustrated in FIG. 7A. Briefly, TIL were electroporated with the test ASO or control ASO, and a mixture of the treated TIL and cognate melanoma cells was transplanted to nude mice, which were monitored for tumor development. The experimental conditions used for the experiments were as follows:

Human TIL (209 clone) were suspended at a concentration $2.5 \times 10^6$ cells to $2.5 \times 10^7$ cells in 1 ml of OptiMem medium, and electroporated with 5 μM either negative control ASO ("TIL control"), or with an ASO corresponding to the nucleic acid sequences of ASO1, modified by 2'-MOE ("TIL ASO"). Electroporation was performed with the following parameters: 260V, 1050 μf, infinite resistance. Cells were incubated in culture medium supplemented with 3000 U/ml IL-2.

24 hours post electroporation, the cells were washed and mixed at a 1:1 ratio with 526mel cells ($1 \times 10^6$ cells each) and immediately injected subcutaneously into the back of 8- to 9-week-old female nude (athymic Foxn1–/–) mice. A second control group was injected with melanoma cells without TIL ("Melanoma only"). Tumor size was measured in two perpendicular diameters three times per week, in the following weeks. The results are presented in FIGS. 7B and 7C.

Figure 7B:
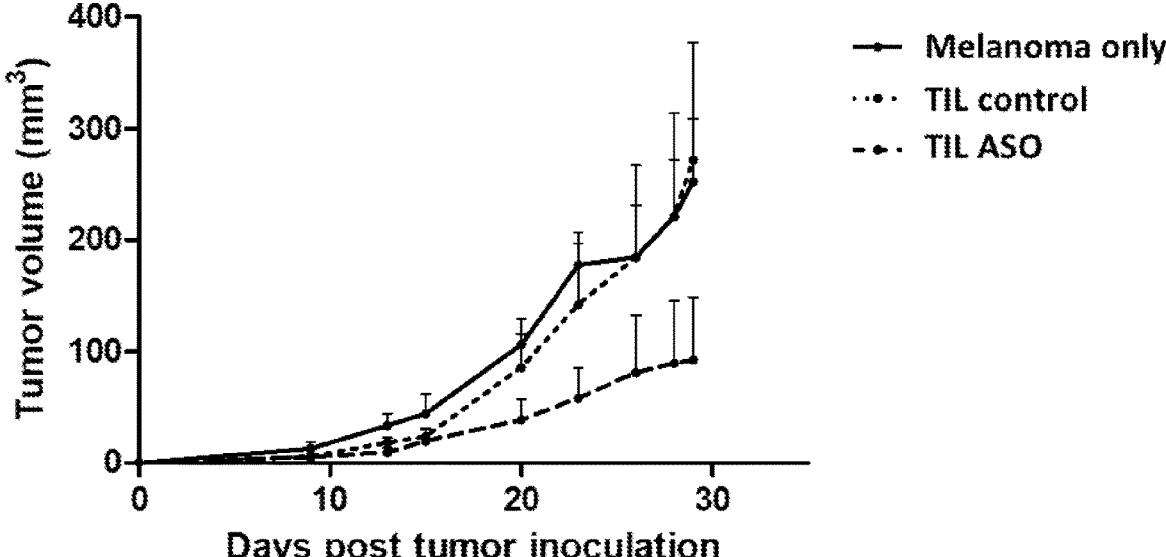
FIG. 7B shows the tumor volume (Mean+SEM) measured over time until day 29, on which the first mouse had to be sacrificed.
Figure 7C:
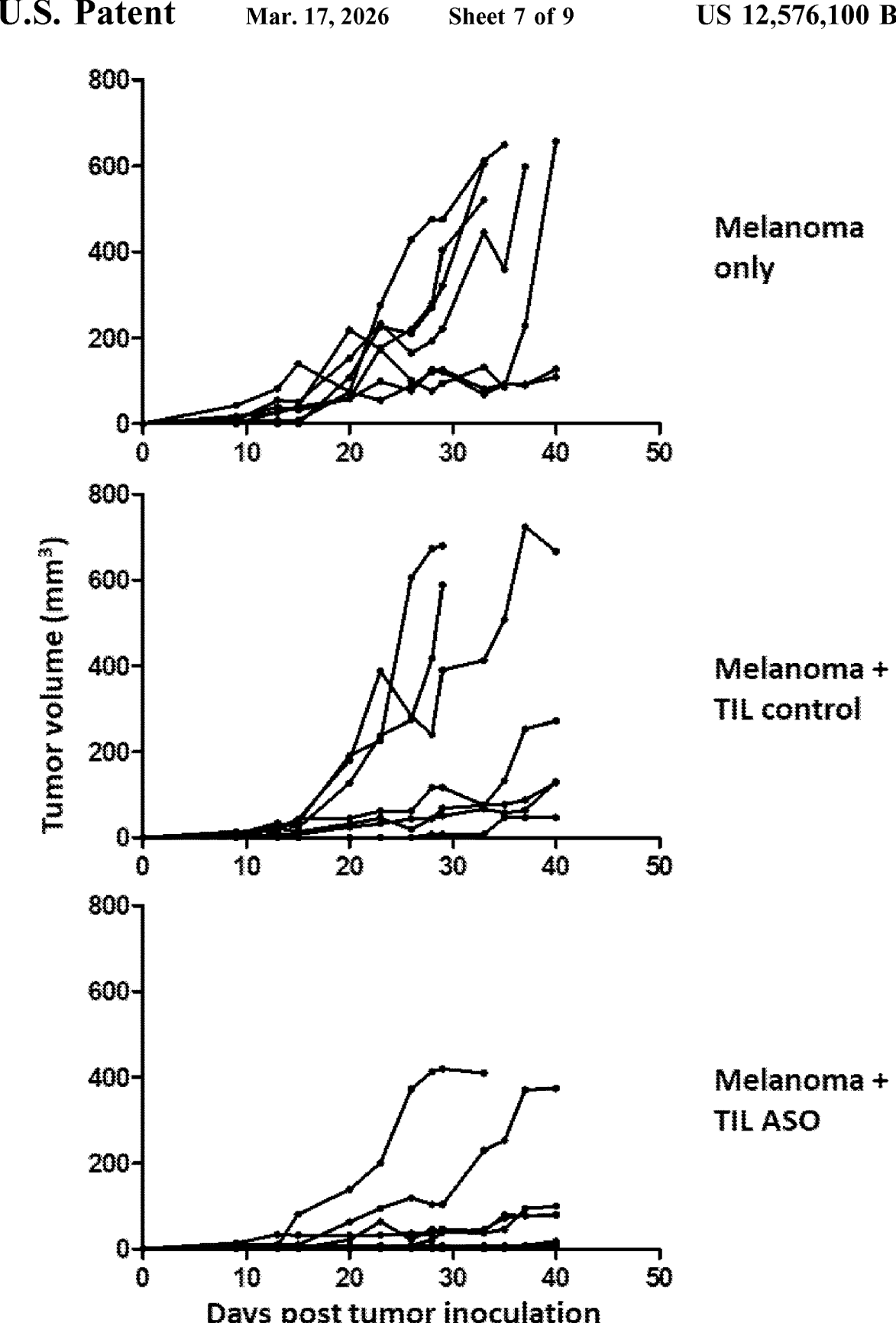
FIG. 7C is a spider plot showing tumor volume of individual mice [calculated as L (length)×W (width)$^2$×0.5].

As can be seen in FIGS. 7B and 7C, the volume of the tumors formed in the presence of SSO-treated TIL was significantly lower than that of the tumors formed in the presence of control TIL, or without co-administered TIL. In addition, as can be seen in FIG. 7C, the tumor cells co-transplanted with SSO-treated TIL either did not develop into measurable tumors, or exhibited an arrest in tumor formation, which ceased to develop beyond an upper threshold.

Example 8. Transcriptional Profile of SSO-Treated T Cells

Wild-type (WT) Jurkat cells were electoporated with 2-MOE modified ASO1 or a control ASO, essentially as described in Example 1. Cells were then activated for 6 hours with a combination of PMA (200 ng/ml) and Ionomycin (300 ng/ml); non-activated cells electroporated with each ASO served as controls. Next, cells were lysed, RNA was extracted, and quantitative RT-PCR was performed with primers directed to various transcription factors, as detailed in Table 1 below.

Data were normalized to HPRT expression in each treatment group, which served as control. The results are presented as relative quantity (RQ), calculating the expression levels from each gene following activation were normalized to their respective levels in the same treatment group prior to activation.

The results are presented in FIGS. 8A-8I, in which "RQ" represents relative quantity after normalization, "0 h" and "6 h" represent the transcription levels before and after activation, respectively, dark columns ("Control") and light columns ("ASO1") represent the expression levels in cells treated by the control ASO or ASO1, respectively. * represents $p < 0.05$ and ** represents $p < 0.01$.

TABLE 1

| Human genes examined in expression assay | | |
|---|---|---|
| Gene | Full name | Primers (SEQ ID NO.)-Forward/Reverse |
| TOX | Thymocyte selection-associated high mobility group box | TTTGACGGTGAGAACATGTA (15) GAATGTTGAAGTCTTCACTTT (16) |
| Eomes | Eomesodermin | TCTTCTTGGATAGAGACACC (17) GCCTTCGCTTACAAGCACTG (18) |
| c-jun | Jun | ATCAAGGCGGAGAGGAAGCG (19) TGAGCATGTTGGCCGTGGAC (20) |
| Runx3 | Runt-related transcription factor 3 | TCATGAAGAACCAGGTGGCC (21) ATGGTCAGGGTGAAACTCTT (22) |
| Tcj7 | Transcription factor 7 | CCAAGTACTATGAGCTGGCC (23) CCTCGACCGCCTCTTCTTC (24) |
| Tbet | T-box transcription factor Tbx21 | AACACGCATATCTTTACTTT (25) TCAATTTTCAGCTGAGTAAT (26) |
| Bcl6 | B-cell lymphoma 6 | TGGCCTGTTCTATAGCATCT (27) TACATGAAGTCCAGGAGGAT (28) |
| Id2 | DNA-binding protein inhibitor ID-2 | GTGAGGTCCGTTAGGAAAAA (29) GTTCATGTTGTATAGCAGGCT (30) |
| Gata3 | Gata3 | TGTGGGCTCTACTACAAGCTTCAC (31) GCTAGACATTTTTCGGTTTCTGGT (32) |

TABLE 1-continued

| | | |
|---|---|---|
| Human genes examined in expression assay | | |
| Gene | Full name | Primers (SEQ ID NO.)- Forward/Reverse |
| HPRT | Hypoxanthine- guanine phosphoribosyl- transferase | GAGGATTTGGAAAGGGTGTTT (33) CATCTCGAGCAAGACGTTCA (34) |

Figure 8A:
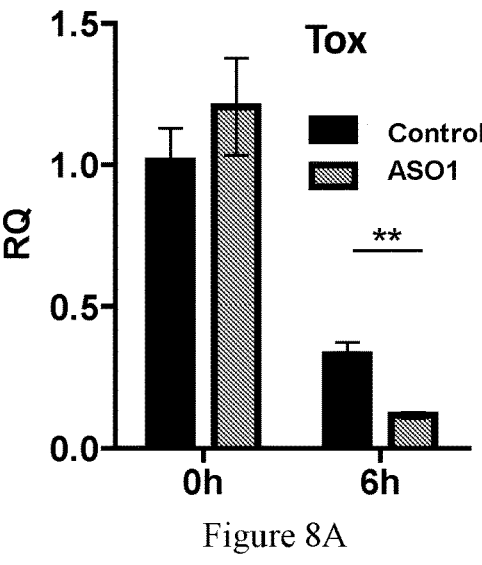
FIGS. 8A-8I show the expression profile of various transcription factors in Jurkat cells electroporated with ASO1 ("ASO1", black columns) or a control ASO ("Control", light columns)
Figure 8B:
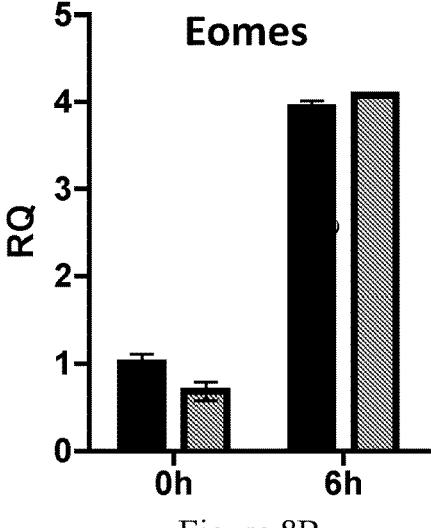
Figure 8C:
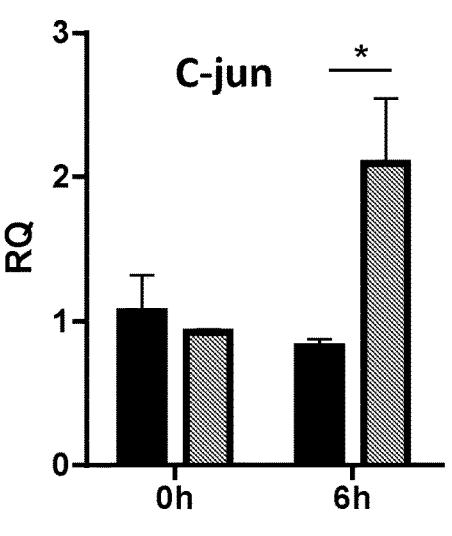
Figure 8D:
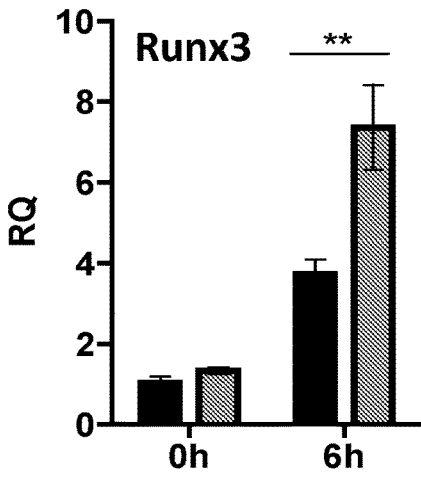
Figure 8E:
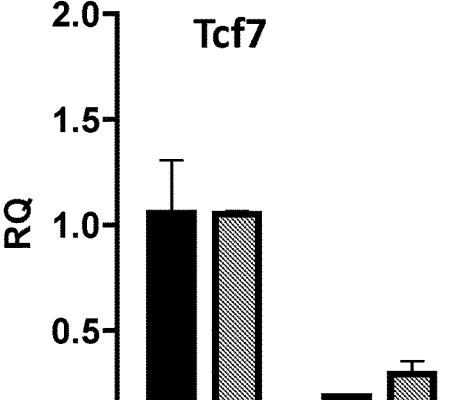
Figure 8F:
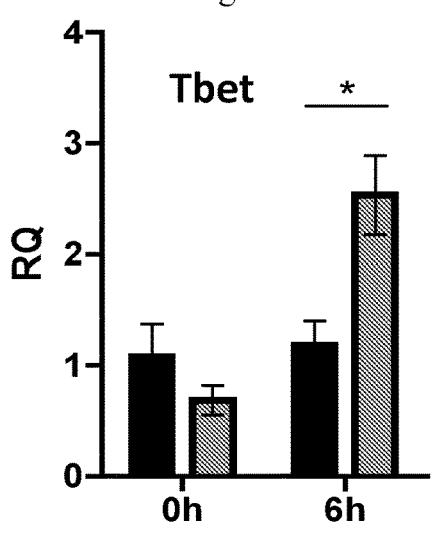
Figure 8G:
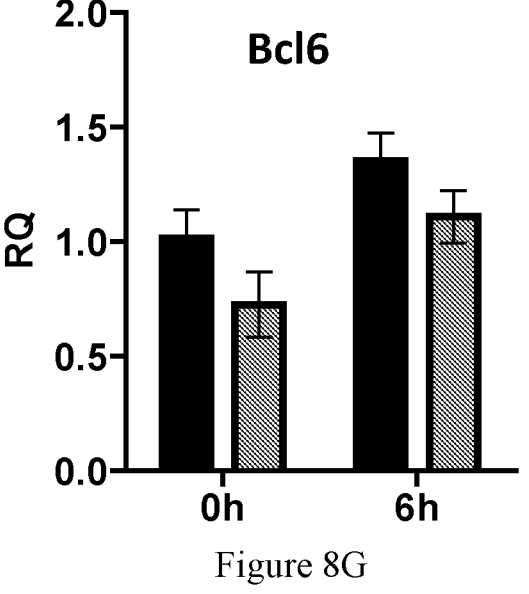
Figure 8H:
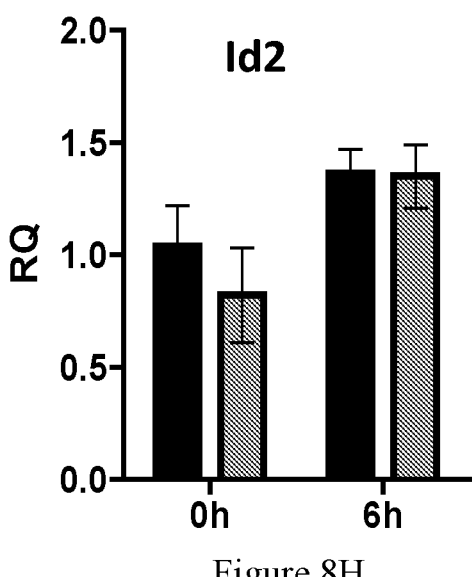
Figure 8I:
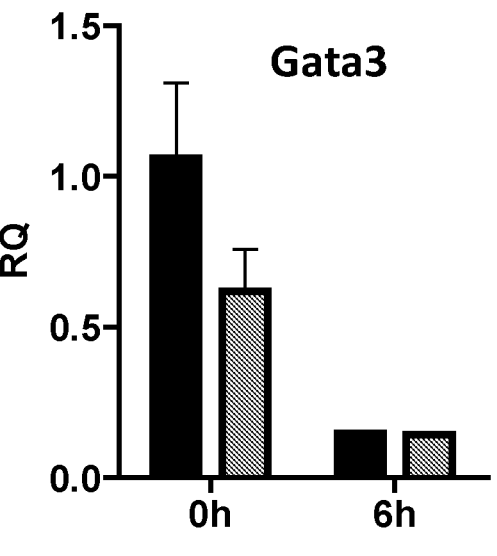

As can be seen in FIGS. 8D, 8C and 8F, the expression of Runx3, C-jun, and Tbet, which typify effector T cell subsets, was significantly up-regulated in ASO1-electroporated Jurkat T cells, while FIG. 8A shows that the expression of TOX, a key regulator of the dysfunctional state, was significantly down-regulated in these cells following activation. In particular, an enhancement of about 1.5-fold in Runx3 expression was measured in activated cells electroporated with ASO1 compared to control, and enhancements by about twofold and 1.7-fold in C-jun, and Tbet expression, respectively, were further measured. In addition, a 3-fold reduction in TOX expression was measured in activated cells electroporated with ASO compared to control.

Thus, the results demonstrate a transcriptional profile that is consistent with enhanced effector T cell functions and reduced T cell exhaustion following SSO treatment.

Example 9. Evaluation of In Vivo Efficacy Against Multiple Tumor Types Using Genetically Engineered Human Lymphocytes NY-ESO-1 (also known as cancer/testis antigen 1, LAGE2 or LAGE2B) is a tumor-associated antigen expressed on many solid tumors, including, but not limited to, synovial sarcoma, melanoma multiple myeloma, neuroblastoma and carcinomas of lung, esophagus, liver, gastrointestinal system, prostate, ovary, breast and bladder. Global data indicates that in the majority of tumors, NY-ESO-1 is frequently expressed in metastatic, high grade/advanced stage tumors, and is as such associated with poor prognosis. A number of pre-clinical studies and clinical trials (completed and ongoing) explore the potential efficacy of immunotherapeutic strategies against NY-ESO-1 expressing tumors.

An in vivo model for evaluating the efficacy of splice-switching ASOs of the invention is performed using lymphocytes genetically engineered to express a TCR directed against NY-ESO-1 in NSG mice employing Winn assay, as follows.

On day 0 of the experiment, human T cells (lymphocytes) are thawed and activated for two days with an anti-CD3 antibody (OKT3, 50 ng/ml) and cultured in culture medium (CM) supplemented with IL-2.

On day 2, lymphocytes are transduced with a vector expressing a TCR directed against NY-ESO-1 collected from producer cells. On day 3 lymphocytes are transferred in culture and grown, and on day 6 a sample is stained with a marker to verify transduction efficiency. On day 6 the transduced cells are further electroporated with an ASO corresponding to the nucleic acid sequences of the invention or a control ASO, as follows. Cells are suspended at a concentration of $2.5 \times 10^6$ cells to $2.5 \times 10^7$ cells in 1 ml of OptiMem medium, and electroporated with 5 µM of either the negative control ASO or test ASO. Electroporation is performed with the following parameters: 260V, 1050 µf, infinite resistance. Cells are then incubated in culture medium supplemented with 3000 U/ml IL-2.

24 hours post electroporation, a mixture (at a ratio of about 1:1) of the treated lymphocyte and NY-ESO-1 expressing tumor cells (selected from the group consisting of: synovial sarcoma, melanoma, multiple myeloma, neuroblastoma and carcinomas of lung, esophagus, liver, gastrointestinal system, prostate, ovary, breast and bladder) is injected subcutaneously into the back of NSG mice ($0.5 \times 10^6$-$2 \times 10^6$ cells per injection). Mice are monitored every two days for weight, general physical condition and tumor volume (by caliper). Mice are sacrificed when tumor volume reaches 1500 mm$^3$.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A SLAMF6 expression-modulating oligonucleotide of 15-30 nucleotides in length, which is a splice-switching oligonucleotide having the nucleic acid sequence of GGGUACUAUGAAGGCAAGAG (SEQ ID NO: 1) or UCAUGGGGUACUAUGAAGGC (SEQ ID NO:2), and wherein said oligonucleotide is a single-stranded RNA molecule, optionally derivatized by one or more backbone and/or sugar chemical modifications.

2. The oligonucleotide of claim 1, which is a single-stranded RNA molecule derivatized by one or more backbone and/or sugar chemical modifications, specifically hybridizable with SEQ ID NO: 6 or 7.

3. The oligonucleotide of claim 2, comprising one or more 2' sugar modifications selected from the group consisting of 2'-O-Methyl (2'-O-Me), 2'-O-methoxyethyl (2'-MOE), and combinations thereof.

4. The oligonucleotide of claim 3, having a nucleic acid sequence selected from the group consisting of SEQ ID NOs: 1 and 2 that is fully derivatized by 2'-O-Me or 2'-MOE.

5. The oligonucleotide of claim 1, having the nucleic acid sequence as set forth in SEQ ID NO: 1, which is derivatized by one or more backbone and/or sugar chemical modifications.

6. The oligonucleotide of claim 1, which modulates the expression of SLAMF6 isoforms in T-cells and enhances anti-tumor immunity of said cells.

7. A nucleic acid construct encoding the oligonucleotide of claim 1.

8. The construct of claim 7, which is an expression vector capable of expressing said oligonucleotide in human T cells.

9. A host cell comprising the construct of claim 8.

10. A pharmaceutical composition comprising the expression-modulating oligonucleotide of claim 1, and optionally a pharmaceutically acceptable carrier, excipient or diluent.

11. A method of treating cancer in a subject in need thereof, comprising administering to the subject, or expressing in cells of said subject, one or more SLAMF6 expression-modulating oligonucleotides as defined in claim 1.

12. The method of claim 11, comprising administering to said subject a synthetic oligonucleotide, having the nucleic acid sequence set forth in any one of SEQ ID NOs: 1 and 2, optionally derivatized by one or more 2' sugar modifications.

13. The method of claim 11, wherein the cancer is selected from the group consisting of melanoma, renal cell carcinoma, lung cancer, breast cancer, and head and neck cancer.

14. The method of claim 11, further comprising administering to the subject a cancer immunotherapy, optionally a T-cell mediated immunotherapy.

15. A method of inducing or enhancing anti-tumor immunity in a subject in need thereof, comprising administering to the subject, or expressing in cells of the subject, one or more SLAMF6 expression-modulating oligonucleotides as defined in claim 1.

16. The method of claim 15, wherein the subject is afflicted with a cancer selected from the group consisting of melanoma, renal cell carcinoma, lung cancer, breast cancer, and head and neck cancer, or further comprising administering to the subject a T-cell mediated cancer immunotherapy.

17. A method of inducing or enhancing splice switching in SLAMF6 expressing cells, comprising administering to, or expressing in the cells, one or more SLAMF6 expression-modulating oligonucleotides as defined in claim 1.

18. The method of claim 17, wherein said cells are T cells, or wherein said method is performed in vitro, or wherein said method is performed in vivo.

19. A method for preparing a T cell composition adapted for adoptive transfer immunotherapy, comprising the step of administering to, or expressing in, a T cell population, one or more SLAMF6 expression-modulating oligonucleotides of claim 1, in an amount and under conditions for inducing or enhancing splice switching in the T cell population.

20. The method of claim 19, comprising:
   a. providing a T cell population comprising CD8$^+$ T cells,
   b. administering to, or expressing in the T cell population, one or more of the SLAMF6 expression-modulating oligonucleotides, in an amount and under conditions for inducing or enhancing splice switching in said T cell population, and
   c. expanding said T cell population, so as to obtain a T cell composition adapted for adoptive transfer immunotherapy comprising an effective amount of the resulting T cell population;
   wherein step c is optionally performed prior to step b, and the T cell containing population is selected from the group consisting of: tumor infiltrating leukocytes (TIL), tumor-specific T cell clones, and genetically modified T cells, or the T cell containing population expresses a chimeric antigen receptor (CAR).

21. A T cell composition adapted for adoptive transfer immunotherapy comprising a T cell population, and the oligonucleotide as defined in claim 1, in an amount and under conditions for inducing or enhancing splice switching in the T cell population.

\* \* \* \* \*